(12) United States Patent
Nakamura et al.

(10) Patent No.: US 11,530,665 B2
(45) Date of Patent: Dec. 20, 2022

(54) DETERIORATION DETERMINATION APPARATUS FOR AMMONIA SENSOR

(71) Applicant: DENSO CORPORATION, Kariya (JP)

(72) Inventors: Satoshi Nakamura, Nisshin (JP); Toshihiko Harada, Nisshin (JP); Kensuke Takizawa, Kariya (JP); Eriko Maeda, Kariya (JP); Hiroaki Yoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 17 days.

(21) Appl. No.: 17/101,542

(22) Filed: Nov. 23, 2020

(65) Prior Publication Data
US 2021/0095611 A1    Apr. 1, 2021

Related U.S. Application Data

(63) Continuation of application No. PCT/JP2019/020083, filed on May 21, 2019.

(30) Foreign Application Priority Data

May 25, 2018  (JP) .............................. JP2018-100252

(51) Int. Cl.
  *F02D 41/22* (2006.01)
  *F01N 3/20* (2006.01)
  *F02D 41/14* (2006.01)

(52) U.S. Cl.
  CPC ......... *F02D 41/222* (2013.01); *F01N 3/2073* (2013.01); *F02D 41/1439* (2013.01); *F01N 2560/021* (2013.01); *F01N 2610/02* (2013.01)

(58) Field of Classification Search
  CPC ............. F02D 41/222; F01N 2560/021; F01N 3/2073; F01N 2610/02; G01N 27/026
  (Continued)

(56) References Cited

U.S. PATENT DOCUMENTS

2010/0326051 A1* 12/2010 Busch ................. F01N 9/00
                                                          60/274
2012/0234077 A1    9/2012 Wang et al.
(Continued)

FOREIGN PATENT DOCUMENTS

EP        1004877 B1 *  1/2009  ........... G01N 27/417
JP        2010-48596 A    3/2010
(Continued)

OTHER PUBLICATIONS

Aug. 20, 2019 International Search Report issued in International Patent Application No. PCT/JP2019/020083.

*Primary Examiner* — Phutthiwat Wongwian
*Assistant Examiner* — Joshua Campbell
(74) *Attorney, Agent, or Firm* — Oliff PLC

(57) ABSTRACT

A deterioration determination apparatus is usable with an ammonia sensor that includes an ammonia element portion that includes, a solid electrolyte, an ammonia electrode, and a reference electrode. The deterioration determining apparatus compares a first evaluation value and a second evaluation value, and determines whether deterioration has occurred in the ammonia element portion of the ammonia sensor at an evaluation time or subsequent to the evaluation time. The first evaluation value is based on a first sensor current obtained when a DC voltage is applied between the ammonia electrode and the reference electrode of the ammonia element portion at an initial time that is during an initial use period of the ammonia sensor. The second evaluation value is based on a second sensor current obtained when the DC voltage is applied between the ammonia electrode and the reference electrode subsequent to the initial period of use of the ammonia sensor.

10 Claims, 12 Drawing Sheets

(58) Field of Classification Search
USPC .......................................................... 123/703
See application file for complete search history.

(56) References Cited

U.S. PATENT DOCUMENTS

| 2017/0167994 | A1* | 6/2017 | Okamoto | ........... G01N 27/4175 |
| 2018/0003119 | A1* | 1/2018 | Aoki | ................... F02D 41/1461 |
| 2018/0180569 | A1* | 6/2018 | Harada | .............. G01N 33/0054 |
| 2018/0252673 | A1* | 9/2018 | Wang | ................ G01N 27/4073 |

FOREIGN PATENT DOCUMENTS

| JP | 2010048596 A | * | 3/2010 | |
| JP | 2011043333 A | * | 3/2011 | ......... G01N 27/4067 |

* cited by examiner

DETERIORATION DETERMINATION APPARATUS FOR AMMONIA SENSOR

CROSS-REFERENCE TO RELATED APPLICATIONS

The present application is a continuation application of International Application No. PCT/JP2019/020083, filed May 21, 2019, which claims priority to Japanese Patent Application No. 2018-100252, filed May 25, 2018. The contents of these applications are incorporated herein by reference in their entirety.

BACKGROUND

Technical Field

The present disclosure relates to a deterioration determination apparatus for an ammonia sensor that determines whether deterioration has occurred in an ammonia sensor.

Related Art

For example, in a vehicle, a catalyst for purifying $NO_X$ (nitrogen oxide), such as NO and $NO_2$, in an exhaust gas that is discharged from a diesel engine or the like is arranged inside an exhaust pipe. The diesel engine or the like serves as an internal combustion engine. In a selective reduction catalyst (selective catalytic reduction [SCR]) that serves as the catalyst, to reduce $NO_X$, ammonia ($NH_3$) that is contained in aqueous urea or the like attaches to a catalyst support. The ammonia and $NO_X$ are chemically reacted in a catalyst support. Reduction of $NO_X$ into nitrogen ($N_2$) and water ($H_2O$) is thereby performed.

In addition, a reducing agent supply apparatus is arranged in a position inside the exhaust pipe further towards an upstream side of a flow of exhaust gas than the selective reduction catalyst is. The reducing agent supply apparatus supplies the selective reduction catalyst with ammonia that serves as a reducing agent. In addition, for example, a $NO_X$ sensor and an ammonia sensor are arranged in positions inside the exhaust pipe that are on a downstream side of the flow of exhaust gas from the selective reduction catalyst. The $NO_X$ sensor detects a $NO_X$ concentration in the exhaust gas. The ammonia sensor detects an ammonia concentration in the exhaust gas. Through use of the $NO_X$ sensor and the ammonia sensor, modification to improve a rate of purification of $NO_X$ by ammonia is achieved while outflow of ammonia from the selective reduction catalyst is suppressed.

SUMMARY

One aspect of the present disclosure provides a deterioration determination apparatus for an ammonia sensor. The deterioration determination apparatus is usable with an ammonia sensor that includes an ammonia element portion that includes a solid electrolyte, an ammonia electrode, and a reference electrode. The deterioration determining apparatus compares a first evaluation value and a second evaluation value, and determines whether deterioration has occurred in the ammonia element portion of the ammonia sensor at an evaluation time or subsequent to the evaluation time. The first evaluation value is based on a first sensor current obtained when a direct-current (DC) voltage is applied between the ammonia electrode and the reference electrode of the ammonia element portion at an initial time that is during an initial period use of the ammonia sensor. The second evaluation value is based on a second sensor current obtained when the DC voltage is applied between the ammonia electrode and the reference electrode subsequent to the initial period of use of the ammonia sensor.

DESCRIPTION OF THE EMBODIMENTS

Figure 1:
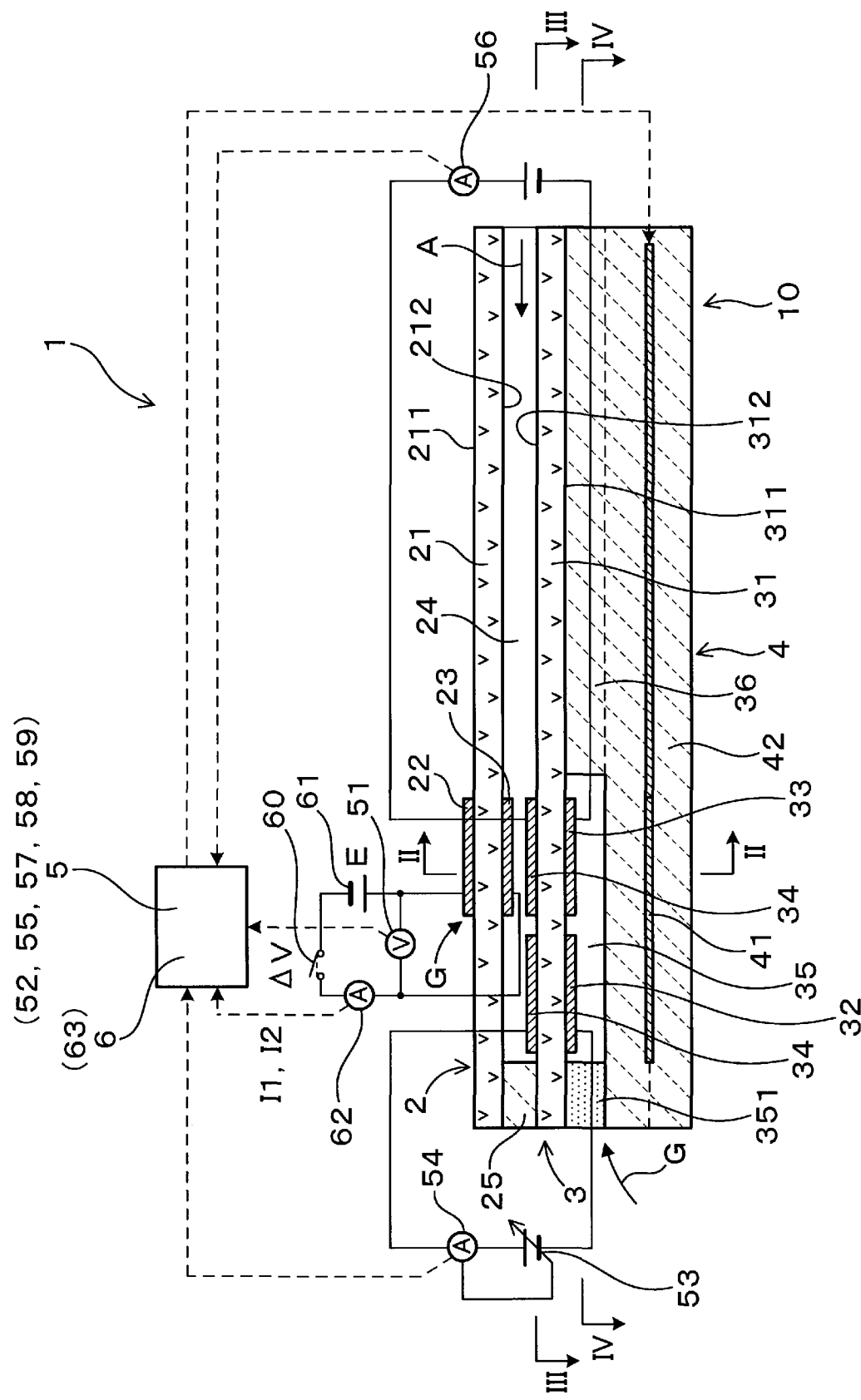
FIG. 1 is an explanatory diagram of configurations of an ammonia sensor and a deterioration determination apparatus according to a first embodiment.

For example, in a diagnosis apparatus in JP-A-2012-193729, to determine validity of a detection value of an ammonia sensor, a comparison of a detection value of a $NO_X$ sensor and the detection value of the ammonia sensor in a fuel non-injected state (fuel-cut state) is performed. When the detection value of the ammonia sensor is determined to be invalid, the detection value of the ammonia sensor is corrected through use of the detection value of the $NO_X$ sensor.

A sensor element of the ammonia sensor is configured to be provided with an ammonia electrode on a surface of a solid electrolyte that is exposed to the exhaust gas and a reference electrode on a side opposite the ammonia electrode with the solid electrolyte therebetween. In addition, for example, in a case of a limiting-current-type ammonia sensor, a voltage is applied between the ammonia electrode and the reference electrode. Furthermore, a flow rate of the exhaust gas that reaches the ammonia electrode is reduced by a diffusion resistance portion. A limiting current that is generated between the pair of electrodes based on the concentration of ammonia is detected.

However, ammonia gas is highly reactive, and may be oxidized or decomposed while the flow rate is being reduced. Therefore, to improve detection accuracy regarding the concentration of ammonia in the exhaust gas, minimizing decrease in the flow rate of the exhaust gas, and enabling the ammonia electrode to more easily come into contact with the exhaust gas can be considered. In this case, a potential-difference-type (electromotive-force-type) ammonia sensor that detects a potential difference that is generated between the ammonia electrode and the reference electrode may be used.

However, in the potential-difference-type ammonia sensor, because the exhaust gas easily comes into contact with the ammonia electrode, a different issue occurs in that the ammonia electrode is poisoned by various toxic substances contained in the exhaust gas and is easily deteriorated. Regarding the potential-difference-type ammonia sensor that has a characteristic such as this in that the ammonia electrode is easily deteriorated, development of an apparatus that is capable of more appropriately determining deterioration that occurs in a sensor element is desired.

Here, in the diagnosis apparatus in JP-A-2012-193729, a specific configuration of an ammonia sensor is not described. Modification for determining deterioration unique to the potential-difference-type ammonia sensor is not described in any way.

The present disclosure has been achieved to provide a deterioration determination apparatus for an ammonia sensor that is capable of appropriately determining whether deterioration has occurred in an ammonia element portion of a potential-difference-type ammonia sensor.

An exemplary embodiment of the present disclosure provides a deterioration determination apparatus for an ammonia sensor. The deterioration determination apparatus is configured to be usable with an ammonia sensor that includes: an ammonia element portion that includes a solid electrolyte that has oxygen ion conductivity, an ammonia electrode that is provided on a first surface of the solid electrolyte that is exposed to a measured gas that contains oxygen and ammonia, and a reference electrode that is provided on a second surface of the solid electrolyte on a side opposite the first surface; a potential difference detecting unit that detects a potential difference between the ammonia electrode and the reference electrode; and an ammonia concentration calculating unit that calculates an ammonia concentration in the measured gas based on the potential difference detected by the potential difference detecting unit.

The deterioration determination apparatus includes: a voltage applying unit that applies a DC voltage between the ammonia electrode and the reference electrode; a current detecting unit that detects a DC current that flows between the ammonia electrode and the reference electrode; and a deterioration determining unit that compares a first evaluation value and a second evaluation value, and determines whether deterioration has occurred in the ammonia element portion at an evaluation time or subsequent to the evaluation time. The first evaluation value is based on a first sensor current that is a DC current that is detected by the current detecting unit obtained when the voltage applying unit applies a DC voltage between the ammonia electrode and the reference electrode at an initial time that is during an initial use period of the ammonia sensor. The second evaluation value is based on a second sensor current that is a DC current that is detected by the current detecting unit obtained when the voltage applying unit applies a DC voltage of a same magnitude as that at the initial time between the ammonia electrode and the reference electrode at the evaluation time that is subsequent to the initial usage period of the ammonia sensor.

The above-described deterioration determination apparatus for an ammonia sensor is used in a potential-difference-type (electromotive-force-type) ammonia sensor and determines whether deterioration has occurred in an ammonia element portion of the ammonia sensor using a sensor current that flows to the ammonia element portion as a result of application of a DC voltage.

The deterioration determination apparatus includes the voltage applying unit, the current detecting unit, and the deterioration determining unit. The deterioration determining unit detects and compares the sensor currents that are obtained when a DC voltage of a same magnitude is applied at the initial time that is the initial period of use of the ammonia sensor and the evaluation time that is subsequent to the initial period of use, and determines whether deterioration has occurred in the ammonia element portion at the evaluation time or subsequent to the evaluation time.

The mixed-potential-type ammonia sensor is ordinarily used without a voltage being applied between the ammonia electrode and the reference electrode, when used to detect the ammonia concentration. At this time, a minute current for detecting the potential difference between the ammonia electrode and the reference electrode flows therebetween. In addition, at the initial time and at the evaluation time, when the voltage applying unit applies the DC voltage between the ammonia electrode and the reference electrode, movement of oxygen ions (oxide ions) suddenly occurs between the ammonia electrode and the reference electrode through the first solid electrolyte. The sensor current flows between the ammonia electrode and the reference electrode.

That is, as a result of the DC voltage being applied between the ammonia electrode and the reference electrode by the voltage applying unit, performance of the ammonia element portion can be reflected in the magnitude of the sensor current. Consequently, particularly in cases in which deterioration has occurred in the ammonia electrode as a result of poisoning or the like, the second sensor current at the evaluation time is thought to becomes less than the first sensor current at the initial time. Therefore, in the deterioration determining unit, as a result of the first evaluation value based on the first sensor current and the second evaluation value based on the second sensor current being compared, whether deterioration has occurred in the ammonia element portion can be appropriately determined.

Consequently, as a result of the above-described deterioration determination apparatus for an ammonia sensor, whether deterioration has occurred in an ammonia element portion of a potential-difference-type (electromotive-force-type) ammonia sensor can be appropriately determined.

Here, the initial time that is the initial period of use of the ammonia sensor may be when use of the ammonia sensor is actually started. Alternatively, the initial time may be when the ammonia sensor is experimentally used before actual use. In addition, the first evaluation value may be a value that is determined for each individual ammonia sensor. Alternatively, the first evaluation value may be a value that is universally determined for ammonia sensors of the same specifications.

Furthermore, the first evaluation value may be a value of the first sensor current or a value that is calculated using the value of the first sensor current. In a similar manner, the second evaluation value may be a value of the second sensor current or a value that is calculated using the value of the second sensor current.

In addition, when the potential difference detecting unit detects the potential difference between the ammonia electrode and the reference electrode during use of the ammonia sensor, a minute voltage can be applied between the ammonia electrode and the reference electrode. In this case, the DC voltage that is applied between the ammonia electrode and the reference electrode by the voltage applying unit for the determination to be performed by the deterioration determining unit can be greater than the minute voltage that is applied during use.

Preferred embodiments of the deterioration determination apparatus for an ammonia sensor, described above, will be described with reference to the drawings.

First Embodiment

As shown in FIG. 1 to FIG. 4, a deterioration determination apparatus 6 for an ammonia sensor 1 according to a present embodiment is used in a potential-difference-type (electromotive-force-type) ammonia sensor 1. The ammonia sensor 1 includes an ammonia element portion 2, a potential difference detecting unit 51, and an ammonia concentration calculating unit 52. The ammonia element portion 2 includes a first solid electrolyte 21, an ammonia electrode 22, and a reference electrode 23. The first solid electrolyte 21 has oxygen-ion conductivity. The ammonia electrode 22 is provided on a first surface 211 of the first solid electrolyte 21 that is exposed to a measured gas G that contains oxygen and ammonia. The reference electrode 23 is provided on a second surface 221 of the first solid electrolyte 21 that is on a side opposite the first surface 211.

As shown in FIG. 1, the potential difference detecting unit 51 is configured to detect a potential difference ΔV that is generated between the ammonia electrode 22 and the reference electrode 23. The ammonia concentration calculating unit 52 is configured to calculate an ammonia concentration in the measured gas G, based on the potential difference ΔV detected by the potential difference detecting unit 51.

As shown in FIG. 1, the deterioration determination apparatus 6 includes a voltage applying unit 61, a current detecting unit 62, and a deterioration determining unit 63. The voltage applying unit 61 is configured to apply a DC voltage E between the ammonia electrode 22 and the reference electrode 23. The current detecting unit 62 is configured to detect sensor currents I1 and I2 that are DC currents that flow between the ammonia electrode 22 and the reference electrode 23. The deterioration determining unit 63 is configured to compare a first evaluation value H1 and a second evaluation value H2, and determine whether deterioration has occurred in the ammonia element portion 2 at an evaluation time or subsequent to the evaluation time. The first evaluation value H1 is based on the first sensor current I1 at an initial time that is an initial period of use of the ammonia sensor 1. The second evaluation value H2 is based on the second sensor current I2 subsequent to the initial period of use of the ammonia sensor 1.

The first sensor current I1 and the second sensor current I2 each refer to the DC current that is detected by the current detecting unit 62 when the DC voltage E is applied between the ammonia electrode 22 and the reference electrode 23 by the voltage applying unit 61. The DC voltages E that are applied by the voltage applying unit 61 when the first sensor current I1 is detected at the initial time and when the second sensor current I2 is detected at the evaluation time are of the same magnitude.

The deterioration determination apparatus 6 for the ammonia sensor 1 according to the present embodiment will be described in detail, below.

(Ammonia Sensor 1)

As shown in FIG. 1, the ammonia sensor 1 according to the present embodiment is a mixed-potential type that is a potential-difference type. In the ammonia sensor 1, the concentration of ammonia in the measured gas G that is in a state in which the measured gas G contains oxygen and ammonia is detected. The potential difference detecting unit 51 according to the present embodiment is configured to detect the potential difference ΔV between the ammonia electrode 22 and the reference electrode 23 that is generated when a reduction current and an oxidation current in the ammonia electrode 22 become equal. The reduction current is generated as a result of an electrochemical reduction reaction (referred to, hereafter, as simply a reduction reaction) of oxygen. The oxidation current is generated as a result of an electrochemical oxidation reaction (referred to, hereafter, as simply an oxidation reaction) of ammonia.

Figure 5:
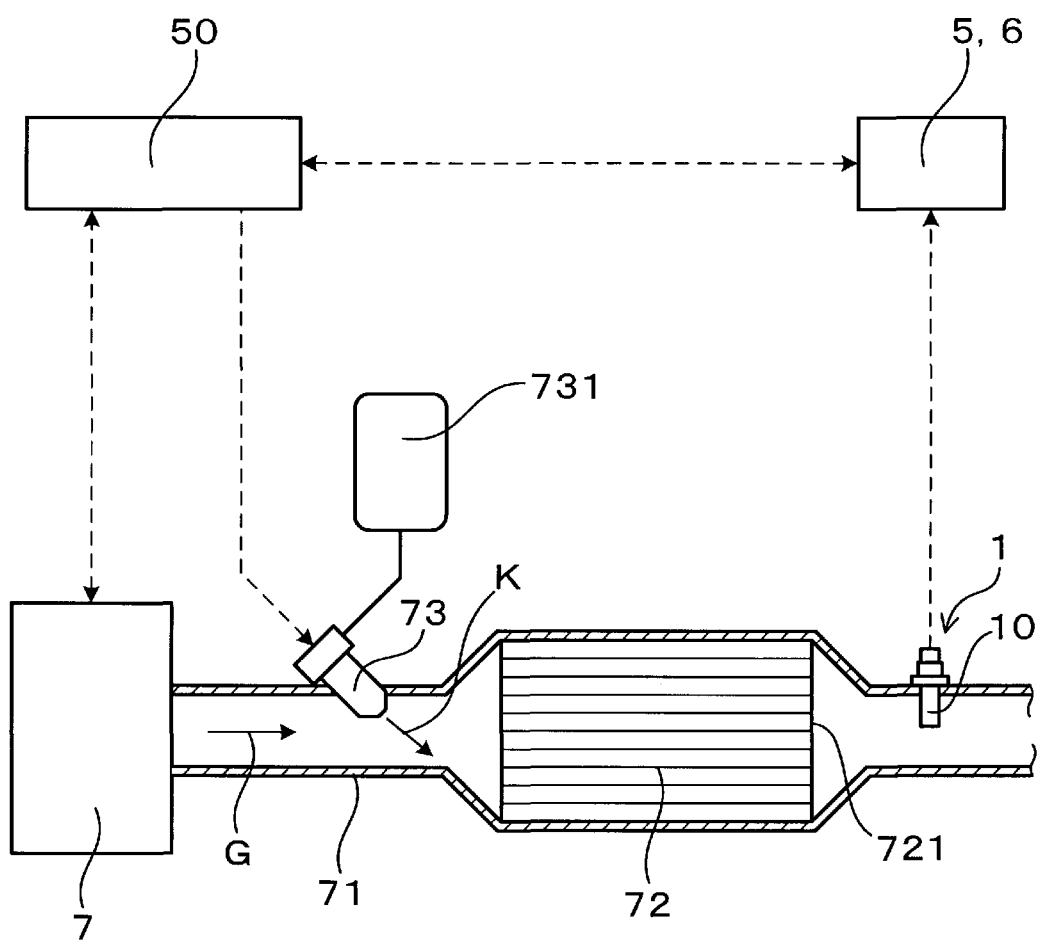
FIG. 5 is an explanatory diagram of a state in which the ammonia sensor and the deterioration determination apparatus are arranged in an internal combustion engine, according to the first embodiment.

As shown in FIG. 5, the ammonia sensor 1 detects the concentration of ammonia that flows out from a catalyst 72 that reduces $NO_X$, in an exhaust pipe 71 of an internal combustion engine (engine) 7 of a vehicle. The measured gas G is an exhaust gas that is discharged from the internal combustion engine 7 to the exhaust pipe 71. A composition of the exhaust gas changes depending on a combustion state in the internal combustion engine 7.

When an air-fuel ratio that is a mass ratio of air and fuel in the internal combustion engine 7 is in a fuel-rich state compared to a theoretical air-fuel ratio, in the composition of the exhaust gas, proportions of HC (hydrocarbon), CO (carbon oxide), $H_2$ (hydrogen), and the like that are contained in unburnt gas increase, whereas a proportion of $NO_X$ (nitrogen oxide) decreases. When the air-fuel ratio in the internal combustion engine 7 is in a fuel-lean state compared to the theoretical air-fuel ratio, in the composition of the exhaust gas, the proportions of HC, CO, and the like decrease, whereas the proportion of $NO_X$ increases. In addition, the measured gas G hardly contains oxygen (air) in the fuel-rich state. The measured gas contains more oxygen (air) in the fuel-lean state.

(Catalyst 72)

As shown in FIG. 5, the catalyst 72 for reducing $NO_X$ and a reducing agent supply apparatus 73 are arranged in the exhaust pipe 71. The reducing agent supply apparatus 73 supplies the catalyst 72 with a reducing agent K that contains ammonia. The catalyst 72 is that in which ammonia that serves as the reducing agent K for $NO_X$ is attached to a catalyst support. An amount of attachment of ammonia to the catalyst support of the catalyst 72 decreases in accompaniment with the reduction reaction of $NO_X$.

In addition, when the amount of attachment of ammonia to the catalyst support decreases, the catalyst support is newly replenished with ammonia from the reducing agent supply apparatus 73. The reducing agent supply apparatus 73 is arranged in a position in the exhaust pipe 71 further towards an upstream side of a flow of exhaust gas than the catalyst 72 is. The reducing agent supply apparatus 73 supplies the exhaust pipe 71 with ammonia gas that is generated by aqueous urea being sprayed. The ammonia gas is generated as a result of the aqueous urea being hydrolyzed. A tank 731 of aqueous urea is connected to the reducing agent supply apparatus 73.

The internal combustion engine 7 according to the present embodiment is a diesel engine that performs combustion operation using self-ignition of light oil. In addition, the catalyst 72 is a selective reduction catalyst (SCR) that causes $NO_X$ (nitrogen oxide) to chemically react with ammonia ($NH_3$) and be reduced to nitrogen ($N_2$) and water ($H_2O$).

Here, although omitted in the drawings, an oxidation catalyst (diesel oxidation catalyst [DOC]) that converts (oxidizes) NO to $NO_2$ and reduces CO, HC (hydrocarbon), and the like, a filter (DPF) that collects particulates, and the like may be arranged in a position in the exhaust pipe 71 on the upstream side of the catalyst 72.

(Multi-Gas Sensor)

As shown in FIG. 5, the ammonia sensor 1 according to the present embodiment is arranged in a position in the exhaust pipe 71 further towards a downstream side than the catalyst 72. Here, strictly speaking, a sensor element 10 and a sensor main body of the ammonia sensor 1 are arranged in the exhaust pipe 71. The sensor main body holds the sensor element 10 For convenience, according to the present embodiment, the sensor main body may be referred to as the ammonia sensor 1.

The ammonia sensor 1 according to the present embodiment is formed as a multi-gas sensor (composite sensor) that is capable of detecting not only the ammonia concentration, but also an oxygen concentration and a $NO_X$ concentration. In addition, the oxygen concentration is used for correcting the ammonia concentration. Furthermore, the ammonia concentration and the $NO_X$ concentration detected by the ammonia sensor 1 are used by an engine control unit (ECU) 50 to determine a timing at which the ammonia that serves as the reducing agent K is supplied to the exhaust pipe 71 from the reducing agent supply apparatus 73. The engine control unit (ECU) 50 serves as a control apparatus of the internal combustion engine 7.

Here, the control apparatus includes various electronic control units, in addition to the engine control unit (ECU) 50 that controls the engine and a sensor control unit 5 that controls the ammonia sensor 1. The control apparatus refers to various types of computers (processing apparatuses).

When the ammonia sensor 1 detects that $NO_X$ is present in the measured gas G, the engine control unit 50 is configured to detect that ammonia is deficient in the catalyst 72, spray aqueous urea from the reducing agent supply apparatus 73, and supply the catalyst 72 with ammonia. Meanwhile, when the ammonia sensor 1 detects that ammonia is present in the measured gas G, the engine control unit 50 is configured to detect that ammonia is excessively present in the catalyst 72, stop the spray of aqueous urea from the reducing agent supply apparatus 73, and stop the supply of ammonia to the catalyst 72. In the catalyst 72, the ammonia for reducing $NO_X$ is preferably supplied without excess or deficiency.

(Relationship Between the Ammonia Concentration and the $NO_X$ Concentration at a Catalyst Exit 721)

As a result of control of ammonia supply by the engine control unit 50 being performed, in a concentration range of $NO_X$ and ammonia in the measured gas G present in the downstream-side position (catalyst exit 721) of the catalyst 72 and an arrangement position of the ammonia sensor 1, a state in which $NO_X$ is appropriately reduced by the ammonia, a state in which an outflow amount of $NO_X$ increases, and a state in which an outflow amount of ammonia increases occur at differing times.

Figure 6:
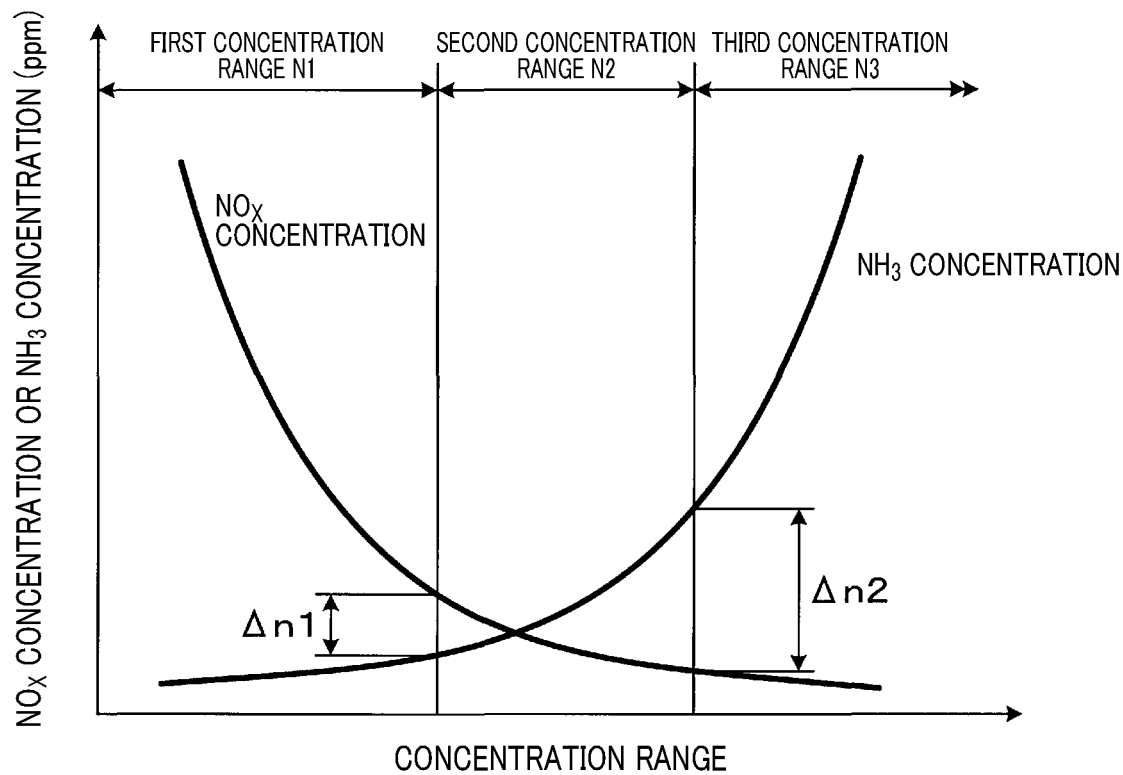
FIG. 6 is an explanatory diagram of concentration regions based on a relationship between an ammonia concentration and a $NO_X$ concentration, according to the first embodiment.

More specifically, as shown in FIG. 6, in the engine control unit 50, the concentration range indicating the relationship between the ammonia ($NH_3$) concentration and the $NO_X$ concentration is divided into a first concentration range N1 in which the $NO_X$ concentration is higher than the ammonia concentration by an amount equal to or greater than a predetermined concentration (first concentration difference $\Delta n1$), a third concentration range N3 in which the ammonia concentration is higher than the $NO_X$ concentration by an amount equal to or greater than a predetermined concentration (second concentration difference $\Delta n2$), and a second concentration range $N_2$ that is between the first concentration range N1 and the third concentration range N3. This concentration range compares the $NO_X$ concentration and the ammonia concentration detected by the ammonia sensor 1 and indicates which of the concentrations is higher in the measured gas G.

Here, a case in which the $NO_X$ concentration is higher than the ammonia concentration by an amount equal to or greater than the predetermined concentration indicates a case in which the $NO_X$ concentration is higher than the ammonia concentration, and a difference between the $NO_X$ concentration and the ammonia concentration is equal to or greater than the first concentration difference $\Delta n1$. In addition, a case in which the ammonia concentration is higher than the $NO_X$ concentration by an amount equal to or greater than a predetermined concentration indicates a case in which the ammonia concentration is higher than the $NO_X$ concentration, and the difference between the ammonia concentration and the $NO_X$ concentration is equal to or greater than the second concentration difference $\Delta n2$. The $NO_X$ concentration that is detected by the ammonia sensor 1 can be considered to include the ammonia concentration because a $NO_X$ electrode 33, described hereafter, detects not only $NO_X$ but also ammonia. Therefore, the $NO_X$ concentration when the $NO_X$ concentration and the ammonia concentration are compared can be a post-correction $NO_X$ concentration that is obtained by the ammonia concentration detected based on the voltage being subtracted from a pre-correction $NO_X$ concentration detected based on the current.

In FIG. 6, in the first concentration range N1 in which the $NO_X$ concentration is high, a small amount of ammonia is presumed to be present in the measured gas G. In the third concentration range N3 in which the ammonia concentration is high, a small amount of $NO_X$ is presumed to be present in the measured gas G. When the reduction reaction of $NO_X$ in the catalyst 72 is more appropriately performed, a state in which ammonia is hardly present in the first concentration range N1 and $NO_X$ is hardly present in the third concentration range N3 is thought to be formed In the division of the concentration ranges, the ammonia concentration and the $NO_X$ concentration are both expressed by % by volume (parts per million [ppm]). The engine control unit 50 can be configured to adjust the amount of the reducing agent K to be supplied to the catalyst 72 from the reducing agent supply apparatus 73 such that the relationship between the ammonia concentration and the $NO_X$ concentration is within the second concentration range $N_2$.

The first concentration difference $\Delta n1$ between the $NO_X$ concentration and the ammonia concentration that serves as the predetermined concentration for dividing the first concentration range N1 and the second concentration range $N_2$ can range from 10 ppm to 50 ppm. In addition, when the $NO_X$ concentration is higher than the ammonia concentration by an amount equal to or greater than 10 ppm to 50 ppm, the engine control unit 50 can determine that the relationship between the ammonia concentration and the $NO_X$ concentration is in the first concentration range N1. The first concentration difference Δn1 can be changed as appropriate based on specifications of the ammonia sensor 1, a mounting environment, and the like.

In addition, the second concentration difference Δn2 between the ammonia concentration and the $NO_X$ concentration that serves as the predetermined concentration for dividing the second concentration range $N_2$ and the third concentration range N3 can range from 50 ppm to 100 ppm. In addition, when the ammonia concentration is higher than the $NO_X$ concentration by an amount equal to or greater than 50 ppm to 100 ppm, the engine control unit 50 can determine that the relationship between the ammonia concentration and the $NO_X$ concentration is in the third concentration range N3. The second concentration difference Δn2 can be changed as appropriate based on the specifications of the ammonia sensor 1, the mounting environment, and the like.

Figure 2:
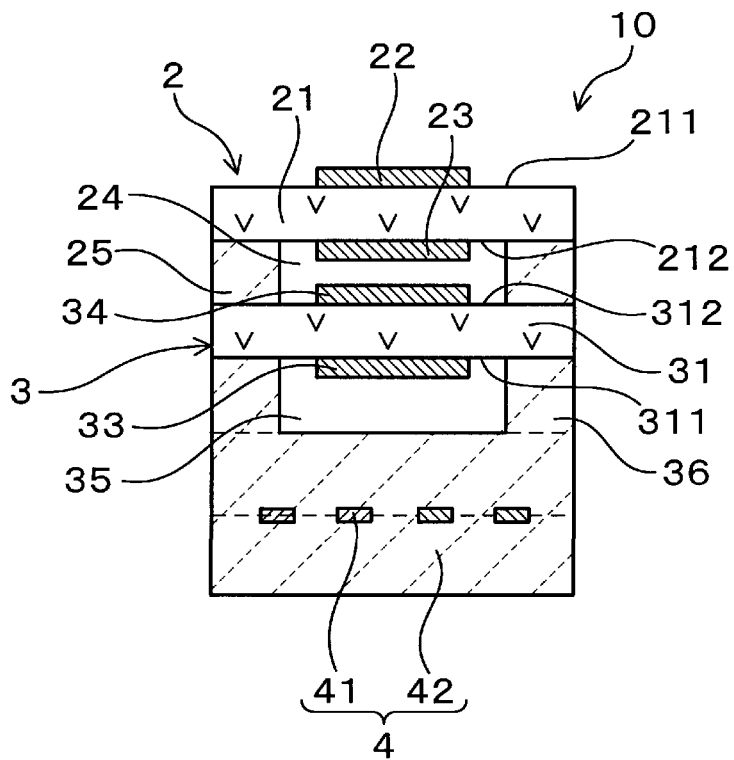
FIG. 2 is a cross-sectional view taken along the line II-II in FIG. 1, showing a sensor element of the ammonia sensor according to the first embodiment.

Although omitted in the drawings, the ammonia sensor 1 includes the sensor element 10, a housing, a tip-end-side cover, and a base-end-side cover. The sensor element 10 is provided to detect the ammonia concentration and the $NO_X$ concentration. The housing is provided to hold the sensor element 10 and attach to the exhaust pipe 71. The tip-end-side cover is attached to a tip-end side of the housing and protects the sensor element 10. The base-end-side cover is attached to a base-end side of the housing and protects an electrical wiring portion of the sensor element 10. As shown in FIG. 1 and FIG. 2, the sensor element 10 is formed by a heater portion 4, described hereafter, being laminated to the ammonia element portion 2 and a $NO_X$ element portion 3, described hereafter.

(Ammonia Element Portion 2)

The first solid electrolyte 21 is formed into a plate shape. The first solid electrolyte 21 is configured using a zirconia material that has a property of conducting oxygen ions in a predetermined temperature range. The zirconia material can be configured by various materials of which zirconia is a main ingredient. As the zirconia material, stabilized zirconia or partially stabilized zirconia in which a portion of the zirconia is replaced by a metallic element of the rare earth group, such as yttria (yttrium oxide), or a metallic element of the alkaline earth group can be used.

The ammonia electrode 22 is configured using a noble metal material, such as gold (Au), a platinum-gold alloy, a platinum-palladium alloy, or a palladium-gold alloy, that has catalytic activity towards ammonia and oxygen. The reference electrode 23 is configured using a noble metal material, such as platinum (Pt), that has catalytic activity towards oxygen. In addition, the ammonia electrode 22 and the reference electrode 23 may contain a zirconia material that serves as a common material for sintering with the first solid electrolyte 21.

As shown in FIG. 1 and FIG. 2, the first surface 211 of the first solid electrolyte 21 that is exposed to the measured gas G forms an outermost surface of the sensor element 10 of the ammonia sensor 1. In addition, a state in which contact with the measured gas Gt is facilitated is formed in the ammonia electrode 22 that is provided on the first surface 211. A protective layer that is composed of a ceramic porous body or the like is not provided on a surface of the ammonia electrode 22 according to the present embodiment. In addition, the measured gas G comes into contact with the ammonia electrode 22 without being diffusion-controlled. Here, a protective layer that minimizes decrease in the flow rate of the measured gas G can be provided on the surface of the ammonia electrode 22.

The second surface 212 of the first solid electrolyte 21 and the reference electrode 23 that is provided on the second surface 212 are exposed to atmospheric air that serves as a reference gas A. An atmospheric air duct (reference gas duct) 24 into which atmospheric air is introduced is formed in an adjoining manner on the second surface 212 of the first solid electrolyte 21.

(Potential Difference Detecting Unit 51)

As shown in FIG. 1, the potential difference detecting unit 51 according to the present embodiment detects the potential difference ΔV between the ammonia electrode 22 and the reference electrode 23 when a mixed potential is generated in the ammonia electrode 22. In the ammonia electrode 22, when ammonia and oxygen are present in the measured gas G that comes into contact with the ammonia electrode 22, the oxidation reaction of ammonia and the reduction reaction of oxygen simultaneously progress.

The oxidation reaction of ammonia is typically expressed by $2NH_3 + 3O_2^- \rightarrow N_2 + 3H_2O + 6e^-$. The reduction reaction of oxygen is typically expressed by $O_2 + 4e^- \geq 2O_2^-$.

In addition, the mixed potential resulting from ammonia and oxygen in the ammonia electrode 22 is generated as a potential when the oxidation reaction (speed) of ammonia and the reduction reaction (speed) of oxygen are equal in the ammonia electrode 22.

Figure 7:
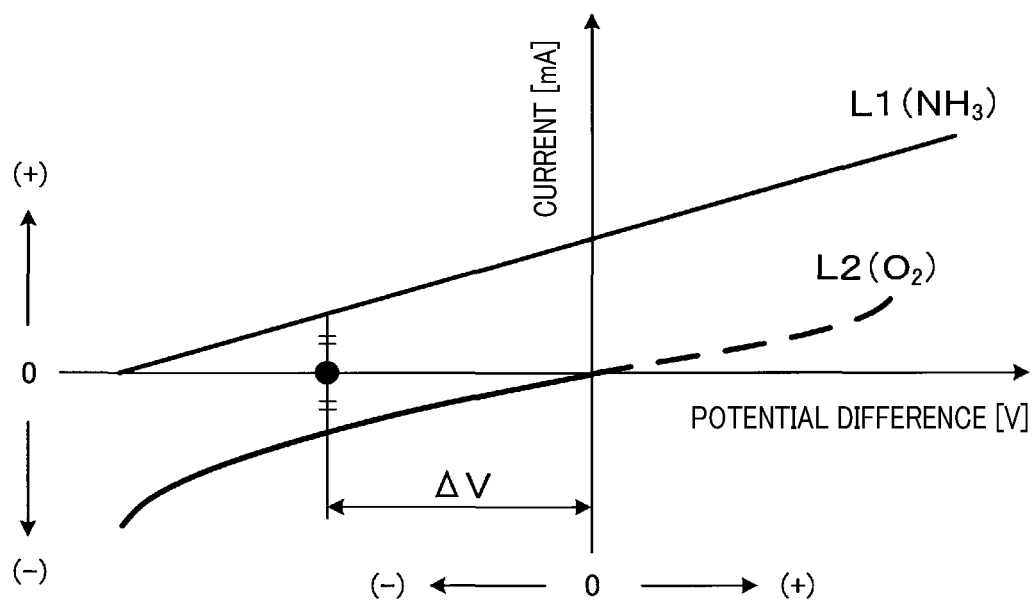
FIG. 7 is an explanatory diagram of mixed potential generated in an ammonia electrode, according to the first embodiment.

FIG. 7 is a diagram for explaining the mixed potential that is generated in the ammonia electrode 22. In FIG. 7, the potential (potential difference ΔV) of the ammonia electrode 22 in relation to the reference electrode 23 is taken on a horizontal axis, the current that flows between the ammonia electrode 22 and the reference electrode 23 is taken on a vertical axis, and a manner in which the mixed potential changes is shown.

In addition, FIG. 7 shows a first line L1 that indicates a relationship between the potential and the current when the oxidation reaction of ammonia is performed in the ammonia electrode 22, and a second line L2 that indicates a relationship between the potential and the current when the reduction reaction of oxygen is performed in the ammonia electrode 2. The first line L1 and the second line L2 are both indicated by lines that rise towards the right.

When the potential difference ΔV is 0 (zero), this indicates that the potential at the ammonia electrode 22 is identical to the potential at the reference electrode 23. The mixed potential is the potential when the current on a positive side on the first line L1 that indicates the oxidation reaction of ammonia and the current on a negative side on the second line L2 that indicates the reduction reaction of oxygen are balanced. In addition, the mixed potential at the ammonia electrode 22 is detected as the potential on the negative side in relation to the reference electrode 23.

Figure 8:
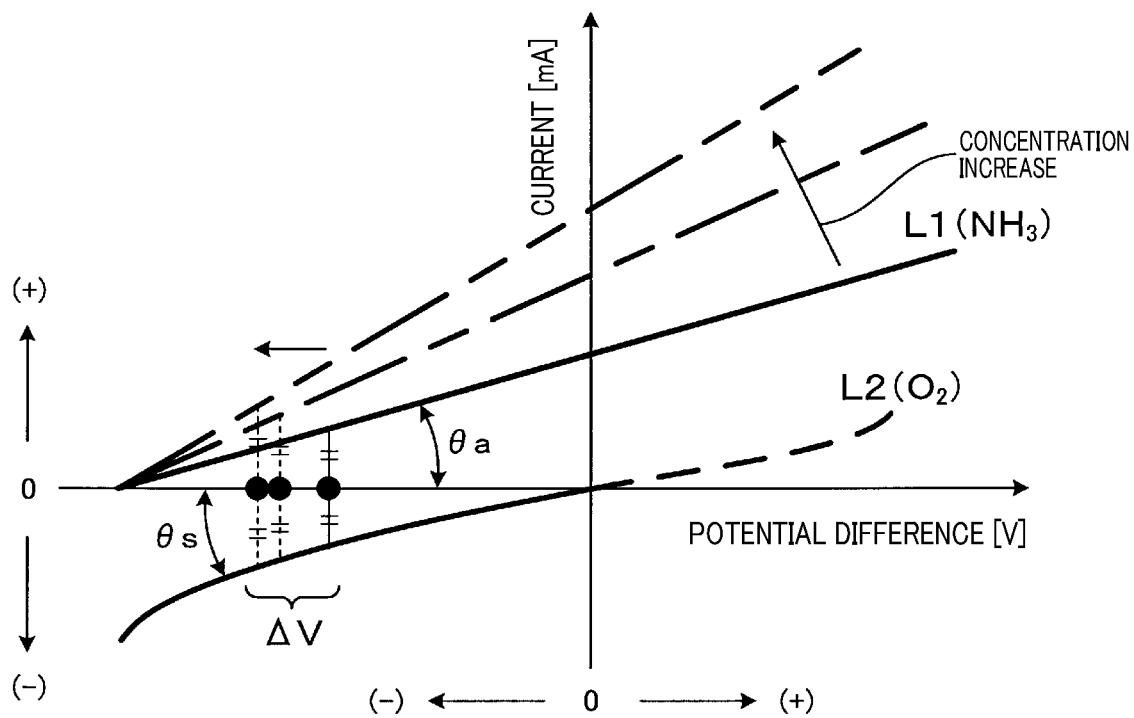
FIG. 8 is an explanatory diagram of mixed potential generated in the ammonia electrode when the ammonia concentration changes, according to the first embodiment.

Furthermore, as shown in FIG. 8, when the ammonia concentration in the measured gas G becomes high, a gradient θa of the first line L1 that indicates the oxidation reaction of ammonia becomes steep. In this case, the potential at which the current on the positive side of the first line L1 and the current on the negative side of the second line L2 become balanced shifts further towards the negative side. As a result, as the ammonia concentration increases, the potential at the ammonia electrode 22 in relation to that at the reference electrode 23 increases towards the negative side.

In other words, as the ammonia concentration increases, the potential difference (mixed potential) ΔV between the ammonia electrode 22 and the reference electrode 23 increases. Consequently, the potential difference ΔV increases as the ammonia concentration increases. As a result of the potential difference ΔV being detected, the ammonia concentration in the measured gas G can be detected.

Figure 9:
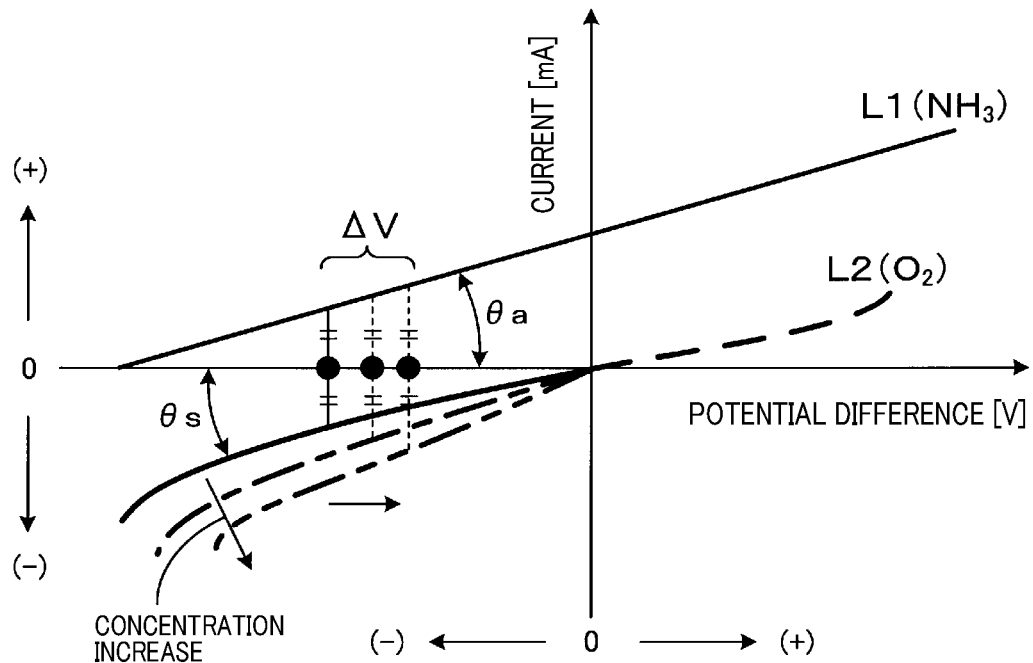
FIG. 9 is an explanatory diagram of mixed potential generated in the ammonia electrode when an oxygen concentration changes, according to the first embodiment.

In addition, as shown in FIG. 9, when the oxygen concentration in the measured gas becomes high, a gradient θs of the second line L2 that indicates the reduction reaction of oxygen becomes steep. In this case, the potential at which the current on the positive side of the first line L1 and the current on the negative side of the second line L2 become balanced shifts to a position that is closer to zero on the negative side.

As a result, as the oxygen concentration increases, the potential on the negative side at the ammonia electrode 22 in relation to the potential at the reference electrode 23 decreases. In other words, as the oxygen concentration increases, the potential difference (mixed potential) ΔV between the ammonia electrode 22 and the reference electrode 23 decreases. Consequently, as the oxygen concentration increases, detection accuracy regarding the ammonia concentration can be improved as a result of correction to increase the potential difference ΔV or the ammonia concentration being performed.

(Ammonia Concentration Calculating Unit 52)

As shown in FIG. 1, the ammonia concentration calculating unit 52 according to the present embodiment is configured to correct the ammonia concentration by using the oxygen concentration that is calculated by an oxygen concentration calculating unit 55, described hereafter, to calculate the ammonia concentration in the measured gas G based on the potential difference ΔV detected by the potential difference detecting unit 51. In the ammonia concentration calculating unit 52, correction to increase the ammonia concentration is performed as the oxygen concentration increases.

Here, the ammonia concentration calculating unit 52 can also be configured to correct the ammonia concentration based on the oxygen concentration and the $NO_X$ concentration. The $NO_X$ electrode 33 in the $NO_X$ element portion 3, described hereafter, not only has catalytic activity towards $NO_X$, but also has catalytic activity towards ammonia. Therefore, the ammonia concentration can be detected as the $NO_X$ concentration in the $NO_X$ electrode 33. As a result, in the ammonia concentration calculating unit 52, the ammonia concentration and the $NO_X$ concentration can be compared, and the ammonia concentration can be corrected to indicate a more correct value.

The potential difference detecting unit 51 and the ammonia concentration calculating unit 52 are formed in the sensor control unit (SCU) 5 that is electrically connected to the ammonia sensor 1. The potential difference detecting unit 51 is formed using an amplifier or the like that measures the potential difference ΔV between the ammonia electrode 22 and the reference electrode 23. The ammonia concentration calculating unit 52 includes a computer or the like. In addition, the sensor control unit 5 is connected to the engine control unit (ECU) 50 of the internal combustion engine 7. The sensor control unit 5 is used for control of operations of the internal combustion engine 7, the reducing agent supply apparatus 73, and the like by the engine control unit 50.

($NO_X$ Element Portion 3)

As shown in FIG. 1, to form the multi-gas sensor, the ammonia sensor 1 according to the present embodiment includes, in addition to the ammonia element portion 2, the potential difference detecting unit 51, and the ammonia concentration calculating unit 52, the $NO_X$ element portion 3, a pump unit 53, a pump current detecting unit 54, the oxygen concentration calculating unit 55, a $NO_X$ detecting unit 56, and a $NO_X$ concentration calculating unit 57. The heater unit 4 that heats the $NO_X$ element portion 3 and the ammonia element portion 2 is laminated to the $NO_X$ element portion 3.

The $NO_X$ element portion 3 includes a second solid electrolyte 31, a measured gas chamber 35, a diffusion resistance portion 351, a pump electrode 32, the $NO_X$ electrode 33, and another reference electrode 34. The second solid electrolyte 31 is arranged so as to oppose the first solid electrolyte 21. The second solid electrolyte 31 is formed into a plate shape. The second solid electrolyte 31 is configured using a zirconia material that has a property of conducting oxygen ions at a predetermined temperature. This zirconia material is similar to that of the first solid electrolyte 21.

Figure 4:
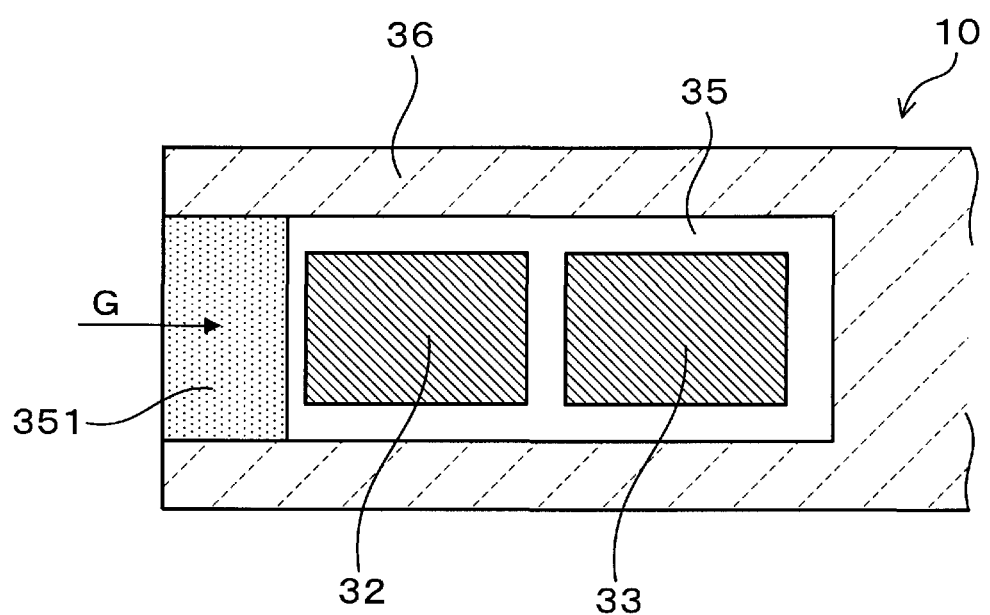
FIG. 4 is a cross-sectional view taken along the line Iv-Iv in FIG. 1, showing the sensor element of the ammonia sensor according to the first embodiment.

As shown in FIG. 1, FIG. 2, and FIG. 4, the measured gas chamber 35 is formed so as to be in contact with a third surface 311 of the second solid electrolyte 31. The measured gas chamber 35 is formed by a gas chamber insulating body 36. The gas chamber insulating body 36 is composed of a ceramic material, such as alumina. The diffusion resistance portion 351 is formed as a porous ceramic layer. The diffusion resistance portion 351 is portion for introducing the measured gas G to the measured gas chamber 35 while limiting diffusion speed.

The pump electrode 32 is housed inside the measured gas chamber 35 on the third surface 311 and exposed to the measured gas G inside the measured gas chamber 35. The $NO_X$ electrode 33 is housed inside the measured gas chamber 35 on the third surface 311 and exposed to the measured gas G after the oxygen concentration is adjusted by the pump electrode 32. The other reference electrode 34 is provided on a fourth surface 312 of the second solid electrolyte 31, on a side opposite the third surface 311.

The pump electrode 32 is configured using a noble metal material, such as a platinum-gold alloy, that has catalytic activity towards oxygen. The $NO_X$ electrode 33 is configured using a noble metal material, such as a platinum-rhodium alloy, that has catalytic activity towards $NO_X$ and oxygen. The other reference electrode 34 is configured using a noble metal material, such as platinum, that has catalytic activity towards oxygen. In addition, the pump electrode 32, the $NO_X$ electrode 33, and the other reference electrode 34 may contain a zirconia material that serves as a common material for sintering with the second solid electrolyte 31.

The other reference electrode 34 according to the present embodiment is provided in each of a position that opposes the pump electrode 32 and a position that opposes the $NO_X$ electrode 33, with the second solid electrolyte 31 therebetween. Here, a single other reference electrode 34 may be provided for the overall positions opposing the pump electrode 32 and the $NO_X$ electrode 33.

Figure 3:
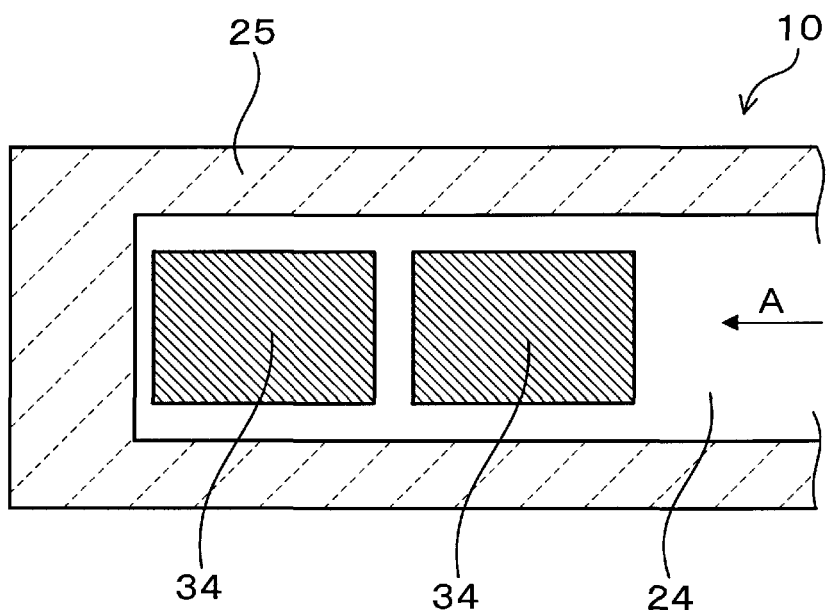
FIG. 3 is a cross-sectional view taken along the line III-III in FIG. 1, showing the sensor element of the ammonia sensor according to the first embodiment.

As shown in FIG. 1 to FIG. 3, the fourth surface 312 of the second solid electrolyte 31 and the other reference electrode 34 that is provided on the fourth surface 312 are exposed to atmospheric air that serves as the reference gas A. The first solid electrolyte 21 and the second solid electrolyte 31 are laminated with a duct insulating body 25 therebetween. The duct insulating body 25 forms the atmospheric duct 24. The duct insulating body 25 is composed of a ceramic material, such as alumina.

The atmospheric duct 24 is formed in a state in which the second surface 212 of the first solid electrolyte 21 and the reference electrode 23, and the fourth surface 312 of the second solid electrolyte 31 and the other reference electrode 34 are in contact with atmospheric air. The reference electrode 23 and the other reference electrode 34 are housed in the atmospheric duct 24. The atmospheric duct 24 is formed from a base end of the sensor element 10 to a position opposing the measured gas chamber 35.

The reference gas A that is introduced into the base-end-side cover of the ammonia sensor 1 is introduced into the atmospheric duct 24 from the opening portion on a base-end side of the atmospheric duct 24. The sensor element 10 according to the present embodiment has the atmospheric duct 24 between the first solid electrolyte 21 and the second solid electrolyte 31. As a result, the overall reference electrode 23 and the other reference electrode 34 can be collectively placed in contact with atmospheric air.

(Heater Unit 4)

As shown in FIG. 1 and FIG. 2, the heater unit 4 that heats the $NO_X$ element portion 3 and the ammonia element portion 2 is laminated on a side of the second solid electrolyte 31 opposite the side on which the first solid electrolyte 21 is laminated. The heater unit 4 is formed by a heat generating body 41 and a heater insulating body 42. The heat generating body 41 generates heat by energization. The heat generation body 41 is embedded in the heater insulating body 42. The heater insulating body 42 is composed of a ceramic material, such as alumina.

The heat generating body 41 is formed by a heat generating portion and a lead portion that is connected to the heat generating portion. The heat generating portion is formed in positions opposing the electrodes 22, 23, 32, 33, and 34. An energization control unit 58 for performing energization of the heat generating body 41 is connected to the heat generating body 41. The energization control unit 58 is formed using a drive circuit or the like that applies a voltage that is subjected to pulse width modulation (PWM) control or the like to the heat generating body 41. The energization control unit 58 is formed in the sensor control unit 5.

A distance between the ammonia element portion 2 and the heater unit 4 is greater than a distance between the $NO_X$ element portion 3 and the heater unit 4. In addition, a temperature at which the heater unit 4 heats the ammonia element portion 2 is lower than a temperature at which the heater unit 4 heats the $NO_X$ element 3. The pump electrode 32 and the $NO_X$ electrode 33 of the $NO_X$ element portion 3 are used in temperatures ranging from 600° C. to 900° C. The ammonia electrode 22 of the ammonia element portion 2 is used in temperatures ranging from 400° C. to 600° C. The temperature of the ammonia element 22 is controlled through heating by the heater unit 4 with any temperature within a temperature range of 400° C. to 600° C. as a target.

In addition, as a result of the atmospheric duct 24 being formed between the $NO_X$ element portion 3 and the ammonia element portion 2, when the heater unit 4 heats the $NO_X$ element portion 3 and the ammonia element portion 2, the atmospheric duct 24 can be made to act as a heat insulating layer. As a result, the temperature of the ammonia electrode 22 of the ammonia element portion 2 can be easily reduced, compared to the temperature of the pump electrode 32 and the $NO_X$ electrode 33 of the $NO_X$ element portion 3. In addition, as a result of energization control by the energization control unit 58 being performed, the temperatures of the $NO_X$ element portion 3 and the ammonia element portion 2 are controlled to target temperatures.

(Pump Unit 53, Pump Current Detecting Unit 54, and Oxygen Concentration Calculating Unit 55)

As shown in FIG. 1, the pump unit 53 is configured to apply a DC voltage between the pump electrode 32 and the other reference electrode 34, with the other reference electrode 34 as the positive side, and pump out the oxygen in the measured gas G inside the measured gas chamber 35.

When the DC voltage is applied between the pump electrode 32 and the other reference electrode 34, the oxygen in the measured gas G inside the measured gas chamber 35 that comes into contact with the pump electrode 32 becomes oxygen ions. The oxygen ions pass through the second solid electrolyte 31 towards the other reference electrode 34 and are discharged from the other reference electrode 34 to the atmospheric duct 24. As a result, the oxygen concentration inside the measured gas chamber 35 is adjusted to a concentration that is suitable for detection of $NO_X$.

The pump current detecting unit 54 is configured to detect a DC current that flows between the pump electrode 32 and the other reference electrode 34. The oxygen concentration calculating unit 55 is configured to calculate the oxygen concentration in the measured gas G based on the DC current detected by the pump current detecting unit 54. In the pump current detecting unit 54, the DC current that is proportional to an amount of oxygen that is discharged from inside the measured gas chamber 35 to the atmospheric duct 24 by the pump unit 53 is detected.

In addition, the pump unit 53 discharges the oxygen from inside the measured gas chamber 35 to the atmospheric duct 24 until the oxygen concentration in the measured gas G inside the measured gas chamber 35 becomes a predetermined concentration. Therefore, the oxygen concentration calculating unit 55 can calculate the oxygen concentration in the measured gas G that reaches the ammonia element portion 2 and the $NO_X$ element portion 3, by monitoring the DC current detected by the pump current detecting unit 54.

The oxygen concentration that is calculated by the oxygen concentration calculating unit 55 is used as the oxygen concentration for correction of the ammonia concentration by the ammonia concentration calculating unit 52.

($NO_X$ Detecting Unit 56 and $NO_X$ Concentration Calculating Unit)

As shown in FIG. 1, the $NO_X$ detecting unit 56 is configured to apply a DC voltage between the $NO_X$ electrode 33 and the other reference electrode 34, with the other reference electrode 34 as the positive side, and detect a DC current that flows between the $NO_X$ electrode 33 and the other reference electrode 34.

The $NO_X$ concentration calculating unit 57 is configured to calculate the pre-correction $NO_X$ concentration in the measured gas G based on the DC current detected by the $NO_X$ detecting unit 56, and calculate the post-correction $NO_X$ concentration by subtracting the ammonia concentration calculated by the ammonia concentration calculating unit 52 from the pre-correction $NO_X$ concentration. In the $NO_X$ detecting unit 56, ammonia is also detected in addition to $NO_X$. Therefore, in the $NO_X$ concentration calculating unit 57, an actual detection amount of $NO_X$ is obtained by a detection amount of ammonia being subtracted.

The $NO_X$ concentration calculated by the $NO_X$ concentration calculating unit 57 has two types. The $NO_X$ concentration that is based on the current that is generated in the $NO_X$ detecting unit 56 is the pre-correction $NO_X$ concentration. The pre-correction $NO_X$ concentration includes the ammonia concentration that is based on ammonia that reacts in the $NO_X$ electrode 33. Meanwhile, the concentration that is obtained by the ammonia concentration calculated by the ammonia concentration calculating unit 52 being subtracted from the pre-correction $NO_X$ concentration calculated by the $NO_X$ concentration calculating unit 57 is the post-correction $NO_X$ concentration. The post-correction $NO_X$ concentration indicates the $NO_X$ concentration from which effects of ammonia are removed. When the ammonia concentration and the $NO_X$ concentration are compared, the post-correction $NO_X$ concentration is used.

The $NO_X$ electrode 33 comes into contact with the measured gas G after the oxygen concentration is adjusted by the pump electrode 32. In addition, in the $NO_X$ detecting unit 56, when the DC voltage is applied between the $NO_X$ electrode 33 and the other reference electrode 34, the $NO_X$ in the measured gas G inside the measured gas chamber 35 that comes into contact with the $NO_X$ electrode 33 is decomposed into nitrogen and oxygen.

The oxygen becomes oxygen ions. The oxygen ions pass through the second solid electrolyte 31 towards the other reference electrode 34 and are discharged from the other reference electrode 34 to the atmospheric duct 24. Furthermore, when the ammonia reaches the $NO_X$ detecting unit 56, the $NO_X$ that is produced by the ammonia being oxidized is similarly decomposed into nitrogen and oxygen.

In addition, the $NO_X$ concentration calculating unit 57 calculates the pre-correction $NO_X$ concentration in the measured gas G that reaches the $NO_X$ element portion 3 by monitoring the DC current that is detected by the $NO_X$ detecting unit 56. The $NO_X$ concentration calculating unit 57 subtracts the ammonia concentration from the pre-correction $NO_X$ concentration and calculates the $NO_X$ concentration as the post-correction $NO_X$ concentration.

In FIG. 6, the $NO_X$ concentration in the concentration ranges that indicate the relationship between the ammonia concentration and the $NO_X$ concentration at the catalyst exit 721 can be considered to be the post-correction $NO_X$ concentration that is calculated by the $NO_X$ concentration calculating unit 57. In addition, the ammonia concentration in the concentration ranges can be considered to be the ammonia concentration that is calculated by the ammonia concentration calculating unit 52.

As a result of the ammonia sensor 1 being the multi-gas sensor that detects not only the ammonia concentration but also the oxygen concentration and the $NO_X$ concentration, when the ammonia concentration and the $NO_X$ concentration are detected, a usage number of gas sensors that are arranged in the exhaust pipe 71 can be reduced. In addition, the oxygen concentration can be detected by the pump current detecting unit 54 and the oxygen concentration calculating unit 55 through use of the pump electrode 32 and the pump unit 53 that are used to detect the $NO_X$ concentration.

The pump unit 53, the pump current detecting unit 54, and the $NO_X$ detecting unit 56 are formed inside the sensor control unit 5 using an amplifier or the like. The oxygen concentration calculating unit 55 and the $NO_X$ concentration calculating unit 57 are formed inside the sensor control unit 5 using a computer or the like.

Here, in FIG. 1, the potential difference detecting unit 51, the pump unit 53, the pump current detecting unit 54, and the $NO_X$ detecting unit 56 are shown separately from the sensor control unit 5, for convenience. In actuality, these components are implemented inside the sensor control unit 5.

(Deterioration Determination Apparatus 6)

As shown in FIG. 1, the deterioration determination apparatus 6 is configured to monitor catalytic performance of the ammonia electrode 22 in the ammonia element portion 2 of the ammonia sensor 1. The deterioration determination apparatus 6 can detect that a malfunction has occurred in the ammonia sensor 1 when a degree of deterioration determined by the deterioration determining unit 63 is large. The deterioration determination apparatus 6 is constructed in the ammonia sensor 1 and the sensor control unit 5 as an additional function.

The deterioration determination apparatus 6 uses the application of DC voltage E in the potential-difference-type ammonia sensor 1 that is used without a direction-current voltage being applied. In the deterioration determination apparatus 6, as a result of the DC voltage E being applied between the ammonia electrode 22 and the reference electrode 23, the sensor currents I1 and I2 are forcibly generated between the ammonia electrode 22 and the reference electrode 23.

In addition, the deterioration determination apparatus 6 according to the present embodiment determines presence/absence of deterioration and a degree of deterioration in the catalytic performance of the ammonia electrode, based on an extent by which the second sensor current I2 at the evaluation time after the ammonia sensor 1 has been used for a certain extended period has decreased compared to the first sensor current I1 before use of the ammonia sensor 1 or at the initial time that is the initial period of use of the ammonia sensor 1.

(Switching Unit 60)

As shown in FIG. 1, the deterioration determination apparatus 6 includes a switching unit 60 for connecting the voltage applying unit 61 and the current detecting unit 62 between the ammonia electrode 22 and the reference electrode 23, when deterioration determination is performed. The switching unit 60 is configured by a switching circuit that connects the voltage applying unit 61 and the current detecting unit 62 between the ammonia electrode 22 and the reference electrode 23 when the deterioration determination apparatus 6 performs the deterioration determination, and separates the voltage applying unit 61 and the current detecting unit 62 from between the ammonia electrode 22 and the reference electrode 23 when the deterioration determination apparatus 6 does not perform the deterioration determination.

(Voltage Applying Unit 61 and Current Detecting Unit 62)

As shown in FIG. 1, the voltage applying unit 61 is configured to apply the DC voltage E between the ammonia electrode 22 and the reference electrode 23 with the reference electrode 23 as the negative side. "Apply the DC voltage E between the ammonia electrode 22 and the reference electrode 23 with the reference electrode 23 as the negative side" means that the voltage is applied with the potential at the reference electrode 23 lower than the potential at the ammonia electrode 22.

The current detecting unit 62 is configured to detect the DC current that flows between the ammonia electrode 22 and the reference electrode 23 when the voltage applying unit 61 applies the DC voltage E. When the potential difference detecting unit 51 detects the potential difference (mixed potential) ΔV, the DC voltage E is not applied between the ammonia electrode 22 and the reference electrode 23, and a minute current flows between the ammonia electrode 22 and the reference electrode 23. Meanwhile, when the voltage applying unit 61 applies the DC voltage E between the ammonia electrode 22 and the reference electrode 23, a large DC current flows between the ammonia electrode 22 and the reference electrode 23. The current detecting unit 62 can then detect the large DC current.

(Direction of Application of the DC Voltage E)

The catalytic performance of the ammonia electrode 22 in the ammonia element portion 2 includes oxidation performance of ammonia and reduction performance of oxygen. In the deterioration determination apparatus 6 according to the present embodiment, the presence/absence of deterioration or the degree of deterioration in the oxidation performance of ammonia in the ammonia electrode 22 is mainly determined. Therefore, in the deterioration determination apparatus 6, the determination regarding the presence/absence of deterioration or the degree of deterioration is performed with times at which the measured gas G contains ammonia as the initial time and the evaluation time.

When the oxidation performance of ammonia in the ammonia electrode 22 is determined, the voltage applying unit 61 of the deterioration determination apparatus 6 preferably applies the DC voltage E that promotes the oxidation reaction of ammonia between the ammonia electrode 22 and the reference electrode 23. Therefore, the voltage applying unit 61 applies the DC voltage E between the ammonia electrode 22 and the reference electrode 23 with the reference electrode 23 as the negative side. In this case, oxygen ions are forcibly supplied from the reference electrode 23 that is exposed to atmospheric air to the ammonia electrode 22. It is thought that the oxidation reaction of ammonia is promoted and a large current flows.

Here, when deterioration in the reduction performance of oxygen in the ammonia electrode 22 is determined, the presence/absence of deterioration or the degree of deterioration is determined with times at which the measured gas G hardly contains ammonia as the initial time and the evaluation time. In this case, it is thought that, regarding the DC voltage E that is applied between the ammonia electrode 22 and the reference electrode 23, either of the ammonia electrode 22 and the reference electrode 23 may be the negative side.

(Effects of Other Gases)

In addition to oxygen, ammonia, and $NO_x$, CO (carbon monoxide), HC (hydrocarbon), and the like that are unburned gas components may be mixed in the exhaust gas that serves as the measured gas G. The mixed potential that is detected at the ammonia electrode 22 is confirmed to not only change based on the ammonia concentration and the oxygen concentration, but also to change based on concentrations of CO, HC, and the like that serve as other gases. However, the changes in the mixed potential due to these other gases are confirmed to hardly occur when ammonia is contained in the measured gas G.

When the measured gas G contains ammonia, the deterioration determination apparatus 6 according to the present embodiment determines the presence/absence of deterioration or the degree of deterioration of the ammonia element portion 2 by applying the DC voltage E between the ammonia electrode 22 and the reference electrode 23 by the voltage applying unit 61. Consequently, the effects that the other gases have on the deterioration determination can be reduced.

(Deterioration Determining Unit 63)

The deterioration determining unit 63 performs the determination regarding deterioration taking into consideration the mixed potential (potential difference $\Delta V$) that is generated between the ammonia electrode 22 and the reference electrode 23, immediately before the DC voltage E is applied between the ammonia electrode 22 and the reference electrode 23 by the voltage applying unit 61.

Figure 10:
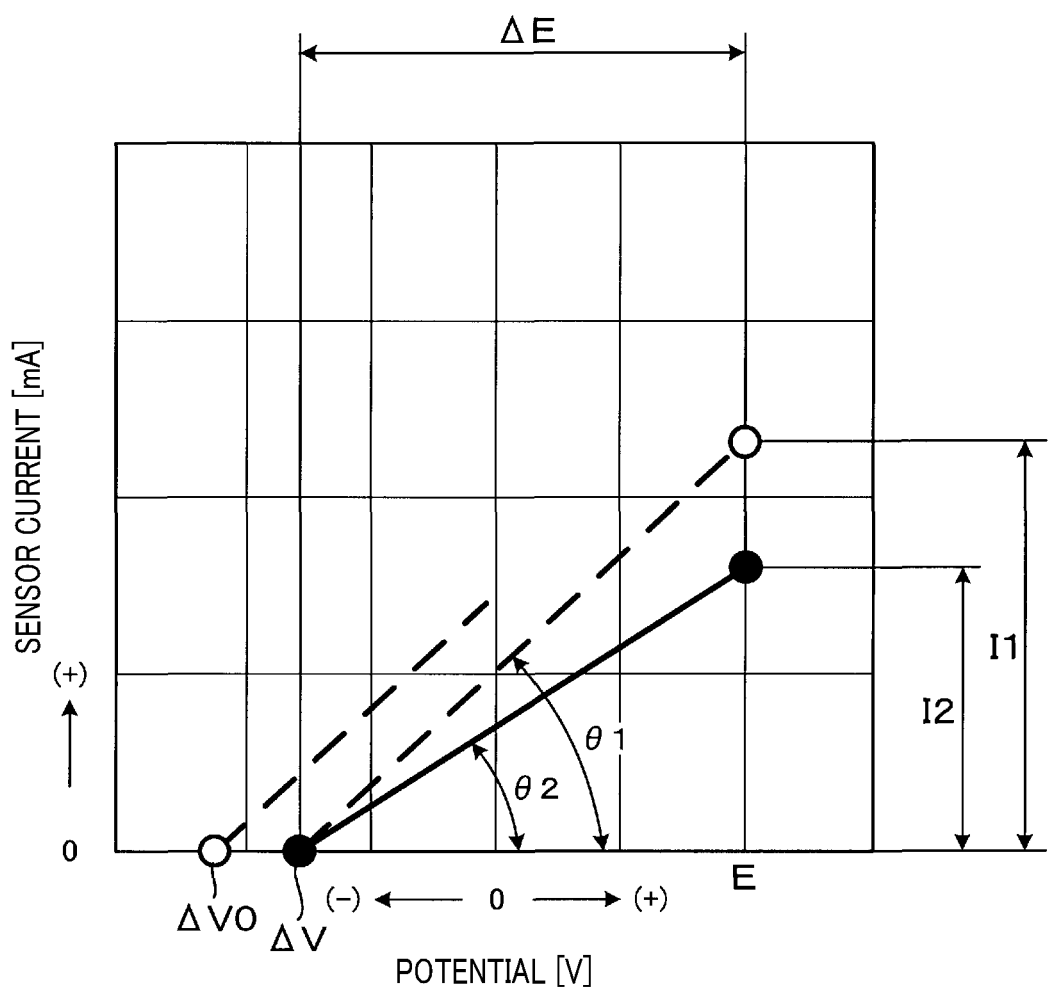
FIG. 10 is an explanatory diagram of a manner by which a first evaluation value and a second evaluation value are compared, according to the first embodiment.

Specifically, as shown in FIG. 10, the deterioration determining unit 63 determines the first evaluation value H1 based on a first difference $\Delta E$ and the first sensor current I1. The first difference $\Delta E$ is obtained by a detected voltage value being subtracted from an applied voltage value. The applied voltage value is the DC voltage E that is applied by the voltage applying unit 61 at the initial time. The detected voltage value is the potential difference $\Delta V$ that is detected by the potential difference detecting unit 51 immediately before the voltage applying unit 61 applies the DC voltage E at the initial time.

The deterioration determining unit 63 according to the present embodiment determines the first evaluation value H1 as a gradient $\theta 1$ (I1/$\Delta F$) that is obtained by the first sensor current I1 being divided by the first difference $\Delta E$. The gradient $\theta 1$ is determined as $\theta 1 = I1/(E-\Delta V)$.

In addition, the deterioration determining unit 63 determines the second evaluation value H2 based on a second difference $\Delta E$ and the second sensor current I2. The second difference $\Delta E$ is obtained by a detected voltage value being subtracted from an applied voltage value. The applied voltage value is the DC voltage E that is applied by the voltage applying unit 61 at the evaluation time. The detected voltage value is the potential difference $\Delta V$ that is detected by the potential difference detecting unit 51 immediately before the voltage applying unit 61 applies the DC voltage E at the evaluation time. The deterioration determining unit 63 according to the present embodiment determines the second evaluation value H2 as a gradient $\theta 2$ (I2/$\Delta E$) that is obtained by the second sensor current I2 being divided by the second difference $\Delta E$. The gradient $\theta 2$ is determined as $\theta 2 = I2/(E-\Delta V)$.

According to the present embodiment, the DC voltage E in which the ammonia electrode 22 is the positive side is applied. Therefore, the first difference (second difference) $\Delta E$ (=E−$\Delta V$) is a sum of the DC voltage E that is a positive component and an absolute value of the potential difference $\Delta V$ that is a negative component.

The potential difference $\Delta V$ when the second evaluation value H2 is determined is preferably made as identical as possible to the potential difference $\Delta V$ when the first evaluation value H1 is determined. That is, as a result of the initial time and the evaluation time being set to times at which the ammonia concentrations are substantially identical, a difference between the ammonia concentrations manifesting as a difference between the first sensor current I1 and the second senor current I2 can be prevented.

In addition, to make the ammonia concentrations in the measured gas G as identical as possible, the initial time and the evaluation time can be set to times at which the operation conditions of the internal combustion engine 7 and the operation state of the reducing agent supply apparatus 73 are as identical as possible. For example, the initial time and the evaluation time can be set to a fuel-cut time of the internal combustion engine 7 or a time at which a predetermined amount of aqueous urea is sprayed from the reducing agent supply apparatus 73 during idling.

The first sensor current I1 can be a current value obtained by convergence when the DC voltage E is applied. Alternatively, the first sensor current I1 can also be a maximum current value that is instantaneously detected when the DC voltage E is applied. This similarly applies to the second sensor current I2.

FIG. 10 shows a manner by which the first evaluation value H1 and the second evaluation value H2 are compared. In FIG. 10, the potential difference [V] of the ammonia electrode 22 in relation to the reference electrode 23 is taken on a horizontal axis. A sensor current [mA] that is generated between the ammonia electrode 22 and the reference electrode 23 is taken on a vertical axis. FIG. 10 shows the gradient θ1 that serves as the first evaluation value H1 and the gradient θ2 that serves as the second evaluation value H2.

In the potential difference detecting unit 51, when the potential at the reference electrode 23 is 0 V, the potential at the ammonia electrode 22 is outputted as a negative voltage. In addition, the voltage applying unit 61 applies the DC voltage E such that the potential at the ammonia electrode 22 is a positive potential. In FIG. 10, the DC voltage E that is applied by the voltage applying unit 61 is indicated as an applied voltage value.

At the evaluation time, when deterioration has hardly occurred in the ammonia element portion 2, the gradient θ2 that serves as the second evaluation value H2 is substantially identical to the gradient θ1 that serves as the first evaluation value H1. As a result, the deterioration determining unit 63 can determine that deterioration has hardly occurred in the ammonia element portion 2. Meanwhile, at the evaluation time, when deterioration has occurred in the ammonia element portion 2, the gradient θ2 that serves as the second evaluation value H2 is less than the gradient θ1 that serves as the first evaluation value H1. As a result, the deterioration determining unit 63 can determine that deterioration has occurred in the ammonia element portion 2.

A reason for using the gradients θ1 and θ2 as the evaluation values H1 and H2 is because of the following consideration. That is, as shown in FIG. 10, when deterioration has occurred in the ammonia element portion 2, the potential difference ΔV detected by the potential difference detecting unit 51 at the evaluation time is outputted to be less than the potential difference ΔV at the actual ammonia concentration. Originally, it is thought that, when the voltage applying unit 61 applies the DC voltage E between the ammonia electrode 22 and the reference electrode 23, the sensor current I2 that is detected by the current detecting unit 62 indicates a greater value as a result of the actual ammonia concentration.

Therefore, as a result of the gradients θ1 and θ2 that are obtained by the sensor currents I1 and I2 being divided by the second difference ΔE between the applied voltage value that is the DC voltage E and the detected voltage value that is the potential difference ΔV being set as the evaluation values, detection accuracy of the deterioration determining unit 63 regarding deterioration can be improved.

According to the present embodiment, the evaluation values H1 and H2 in which the magnitude of the mixed potential immediately before the DC voltage E is applied is taken into consideration and the difference in the ammonia concentrations at the initial time and the evaluation time is taken into consideration are determined. Consequently, accuracy of the determination regarding deterioration of the ammonia element portion 2 can be improved.

The initial time can be set to be immediately after use of the ammonia sensor 1 is actually started or within a predetermined period after use is started. The evaluation time can be set as a predetermined set period during which the presence/absence or the degree of deterioration of the ammonia element portion 2 is to be evaluated.

The deterioration determination by the deterioration determining unit 63 can be performed at the evaluation time. In addition, at the evaluation time, the current detecting unit 62 can detect the second sensor current I2 and, subsequent to the evaluation time, the deterioration determining unit 63 can compare the first evaluation value H1 and the second evaluation value H2 and perform the deterioration determination of the ammonia element portion 2.

The deterioration determining unit 63 can detect the degree of deterioration of the ammonia element portion 2 by a degree of decrease in the second evaluation value H2 in relation to the first evaluation value H1. In addition, when a rate of decrease in the second evaluation value H2 in relation to the first evaluation value H1 exceeds a predetermined threshold, the deterioration determining unit 63 can detect that deterioration has occurred in the ammonia element portion 2.

Figure 11:
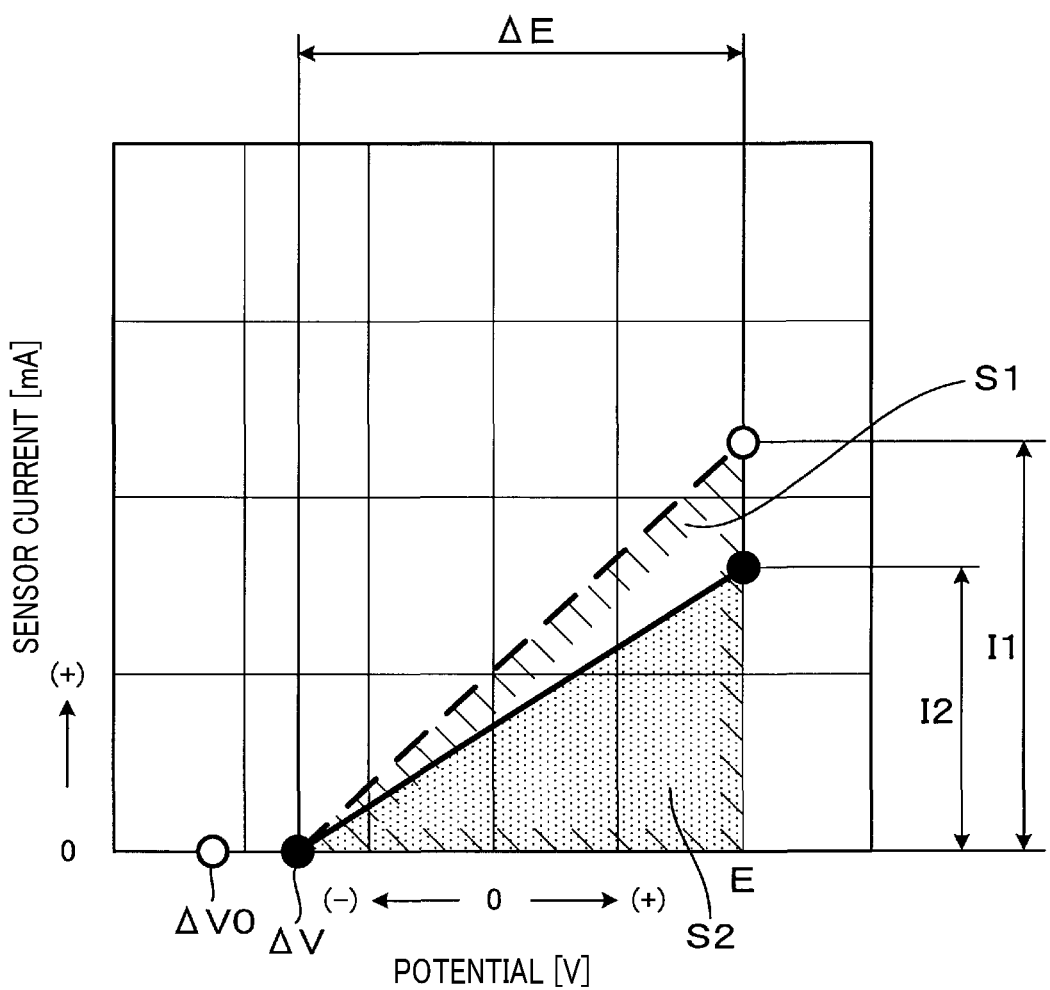
FIG. 11 is an explanatory diagram of another manner by which the first evaluation value and the second evaluation value are compared, according to the first embodiment.

Furthermore, as shown in FIG. 11, the deterioration determining unit 63 may determine the first evaluation value H1 based on an area S1 that is obtained by multiplying the first difference ΔE and the first sensor current I1. In addition, the deterioration determining unit 63 may determine the second evaluation value H2 based on an area S2 that is obtained by multiplying the second difference ΔF and the second sensor current I2. Here, the areas S1 and S2 can respectively be ½ of the products of the differences ΔE and the sensor currents I1 and I2. In addition, the first evaluation value H1 and the second evaluation value H2 can also be determined based on criteria other than the gradients θ1 and θ2 or the areas S1 and S2, through use of the differences ΔE and the sensor currents I1 and I2.

In addition, the deterioration determining unit 63 can also determine a plurality of second evaluation values H2 with a plurality of points in time at which the ammonia concentrations calculated by the ammonia concentration calculating unit 52 differ, as the evaluation times. The deterioration determining unit 63 can then successively compare the first evaluation value H1 and each of the plurality of second evaluation values H2, and determine the presence/absence or the degree of deterioration of the ammonia element portion 2. In this case, accuracy of the deterioration determination can be further improved.

The voltage applying unit 61, the current detecting unit 62, and the deterioration determining unit 63 are formed inside the sensor control unit 5. The voltage applying unit 61 is configured using a DC power supply or the like. The current detecting unit 62 is formed using an amplifier or the like that measures the current that flows between the ammonia electrode 22 and the reference electrode 23. The deterioration determining unit 63 is formed using a computer or the like.

(Setting of Timings at which to Perform the Deterioration Determination)

The initial time in the deterioration determining unit 63 is set to be during the initial period of use of the ammonia sensor 1 and when the ammonia concentration calculated by the ammonia concentration calculating unit 52 is a concentration that indicates the detection of ammonia. In addition, the evaluation time in the deterioration determining unit 63 is set to be subsequent to the initial period of use of the ammonia sensor 1 and when the ammonia concentration calculated by the ammonia concentration calculating unit 52 is a concentration that indicates the detection of ammonia. When the concentration ranges that indicate the relationship between the ammonia concentration and the $NO_X$ concentration in FIG. 6 are used, the initial time and the evaluation time are set to when the relationship is in the second concentration range $N_2$ or the third concentration range N3.

The mixed-potential-type ammonia sensor 1 has a characteristic in that, as the ammonia concentration in the measured gas G increases, the mixed potential detected by the potential difference detecting unit 51 is easily saturated, and the mixed potential does not easily change. When the ammonia concentration in the measured gas G is low, a slight difference in the ammonia concentration can be easily outputted as a change in the mixed potential. Conversely, when the ammonia concentration in the measured gas G becomes high, even when the ammonia concentration significantly changes, the change is not easily outputted as a change in the mixed potential.

In FIG. 8, when the ammonia concentration in the measured gas G becomes high, the gradient of a first line L1 that indicates the oxidation reaction of ammonia becomes steep. In addition, as the gradient of the first line L1 becomes steeper, while the potential difference $\Delta V$ between the ammonia electrode 22 and the reference electrode 23 increases, the amount of change in the potential difference $\Delta V$ decreases.

In general, detection accuracy regarding the ammonia concentration increases as the ammonia concentration decreases. Therefore, when the detection accuracy regarding the ammonia concentration is taken into consideration, a range of the ammonia concentration over which the deterioration determination by the deterioration determination apparatus 6 is performed is preferably when the ammonia concentration is detected at a concentration that is not excessively high.

The initial time and the evaluation time can be set to when the ammonia is detected at an appropriate concentration in the ammonia sensor 1. The deterioration determining unit 63 can determine the initial time and the evaluation time under a condition that the ammonia concentration calculated by the ammonia concentration calculating unit 52 is a concentration that indicates the detection of ammonia and is a concentration that is equal to or less than 200 [ppm]. In this case, the accuracy of the determination by the deterioration determination apparatus 6 can be improved. For example, the concentration that indicates the detection of ammonia can be set to 5 [ppm].

Figure 12:
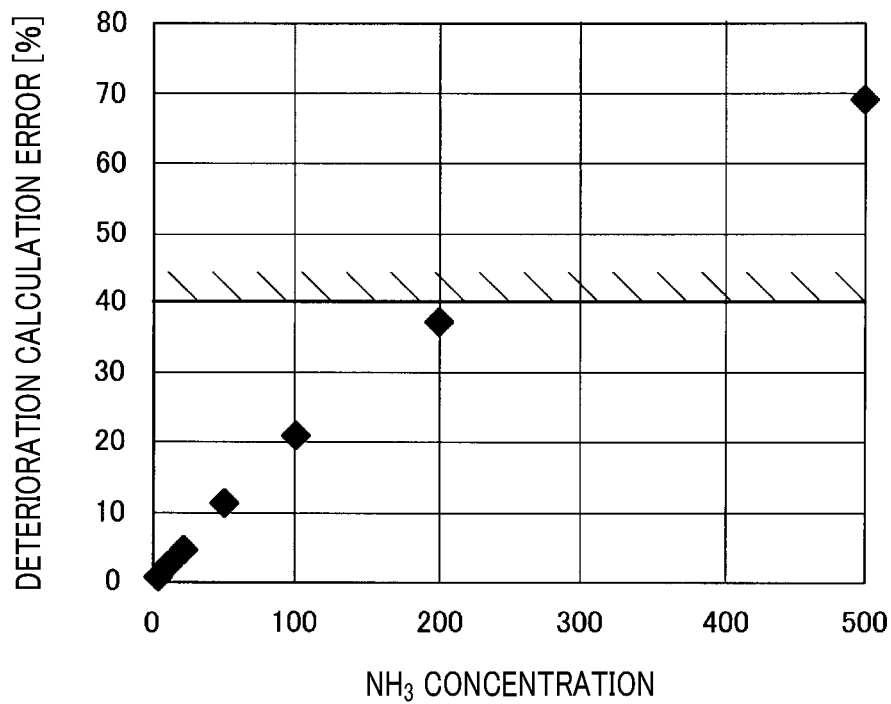
FIG. 12 is a graph of a relationship between the ammonia concentration and a deterioration calculation error, according to the first embodiment.

FIG. 12 shows effects on a deterioration calculation error caused by differences in the magnitude of the ammonia concentration calculated by the ammonia concentration calculating unit 52. The deterioration calculation error is an error that occurs in the calculation of the degree of deterioration (deterioration amount) of the ammonia element portion 2 by the deterioration determining unit 63. The deterioration calculation error refers to an error variation that occurs in a value that is calculated as the deterioration amount when the ammonia concentration varies by 10 [%].

In addition, to set the error variation in the deterioration amount that is allowed when the degree of deterioration is calculated to be equal to or less than 40 [%], the ammonia concentration is required to be equal to or less than 200 [ppm]. Here, a reason for setting a variation amount of the ammonia concentration to 10 [%] is because detection accuracy of the ammonia sensor 1 regarding the ammonia concentration is presumed to be ±10 [%].

The deterioration determining unit 63 can set the initial time and the evaluation time for determining the presence/absence and the degree of deterioration of the ammonia element portion 2 in a following manner.

The deterioration determining unit 63 can determine the initial time and the evaluation time with a period during which the reducing agent supply apparatus 73 supplies the catalyst 72 with the reducing agent K as a condition. When the reducing agent supply apparatus 73 supplies the catalyst 72 with the reducing agent K, in the catalyst 72, an increase in ammonia that is not used to reduce the $NO_X$ is assumed. In this case, ammonia being detected in the ammonia sensor 1 is assumed. Therefore, the initial time and the evaluation time can be set to this period.

In addition, the deterioration determining unit 63 can also determine the initial time and the evaluation time with a period during which the internal combustion engine 7 performs a fuel-cut operation and the reducing agent supply apparatus 73 supplies the reducing agent K as a condition. During fuel-cut, combustion of fuel in the internal combustion engine 7 is stopped, and discharge of $NO_X$ from the internal combustion engine 7 to the exhaust pipe 7 hardly occurs.

Furthermore, the catalyst 72 is filled with the oxygen contained in atmospheric air. In this state, when the ammonia that serves as the reducing agent K is supplied to the catalyst 72 from the reducing agent supply apparatus 73, the ammonia easily reaches the ammonia sensor 1 from the catalyst 72. Therefore, the initial time and the evaluation time can be set in this period.

An amount of discharge of $NO_X$ to the exhaust pipe 71 changes as appropriate based on a rotation speed, a fuel injection amount, the air-fuel ratio, and the like of the internal combustion engine 7. In general, when the rotation speed of the internal combustion engine 7 increases, the fuel injection amount is appropriately reduced, and the air-fuel ratio is in a lean state in relation to a theoretical air-fuel ratio, the amount of discharge of $NO_X$ increases. In addition, operation of the internal combustion engine 7 is performed, and a relationship map of the rotation speed, the fuel injection amount, the air-fuel ratio, and the like of the internal combustion engine 7 and the amount of discharge of $NO_X$ is generated. Furthermore, a ratio of NO and $NO_2$ in the exhaust gas is also taken into consideration regarding the amount of discharge of $NO_X$.

In addition, after the operation of the internal combustion engine 7 is started, when the initial time or the evaluation time is determined, the rotation speed, the fuel injection amount, the air-fuel ratio, and the like of the internal combustion engine 7 at a current time are collated with the relationship map. The amount of discharge of $NO_X$ that takes into consideration the ratio of NO and $NO_2$ is read. A theoretical amount of ammonia for reducing the $NO_X$ is determined.

Furthermore, an amount of generated ammonia that is generated is determined from an amount of injection of aqueous urea by the reducing agent supply apparatus 73 at the current time. Then, when the amount of generated ammonia is greater than the theoretical amount of ammonia by an amount that is equal to or greater than a predetermined amount, the initial time and the evaluation time can be set.

(Deterioration Determination Method)

Next, an example of a method for performing deterioration determination control using the deterioration determination apparatus 6 will be described with reference to flowcharts in FIG. 13 and FIG. 14.

When the combustion operation of the internal combustion engine 7 is started, the ammonia sensor 1, the reducing agent supply apparatus 73, the deterioration determination apparatus 6, and the like are operated. In the ammonia sensor 1, the potential difference detecting unit 51 detects the potential difference $\Delta V$ that is generated between the ammonia electrode 22 and the reference electrode 23. In addition, the pump electrode detecting unit 54 detects the DC current that flows between the pump electrode 32 and the other reference electrode 34.

Furthermore, the oxygen concentration calculating unit 55 calculates the oxygen concentration in the measured gas G based on the DC current detected by the pump current detecting unit 54. In addition, the ammonia concentration calculating unit 52 calculates the ammonia concentration in the measured gas G based on the potential difference ΔV detected by the potential difference detecting unit 51. Furthermore, the ammonia concentration calculating unit 52 corrects the ammonia concentration based on the oxygen concentration calculated by the oxygen concentration calculating unit 55.

Figure 13:
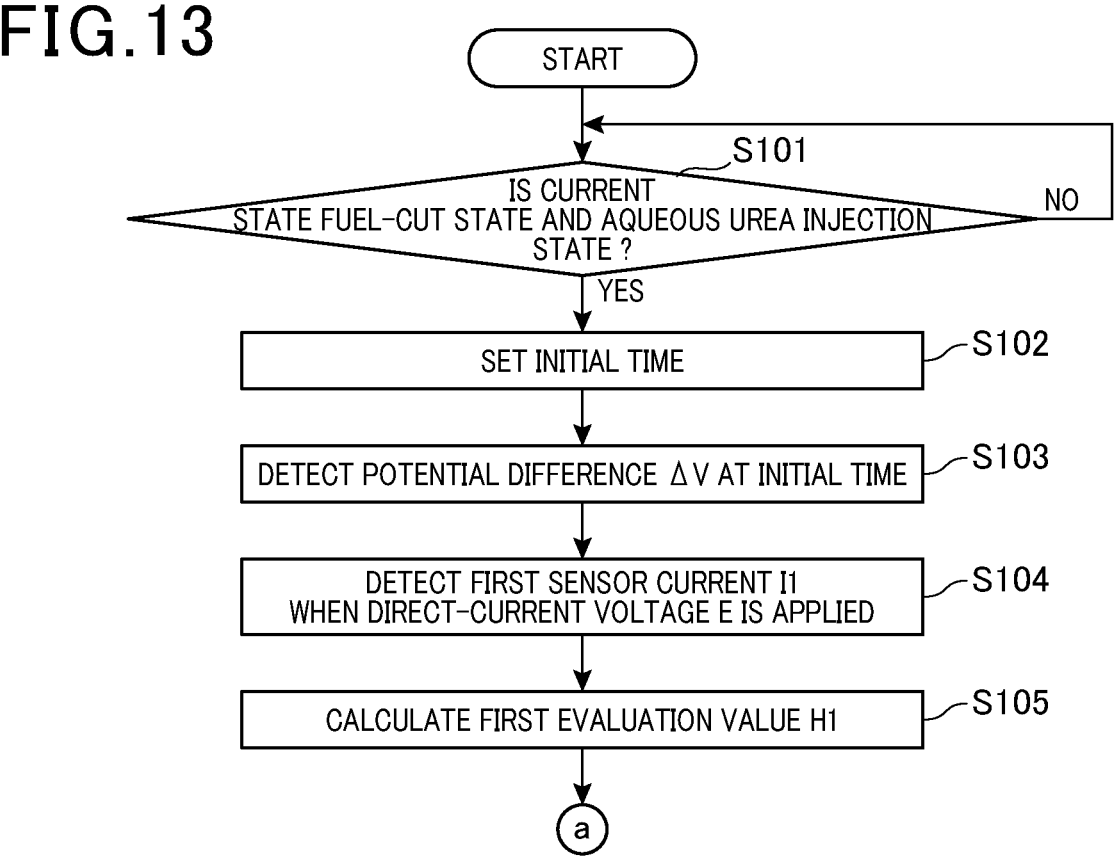
FIG. 13 is a flowchart of a deterioration determination method of the deterioration determination apparatus, according to the first embodiment.

Next, to select a case in which ammonia is detected by the ammonia sensor 1, the deterioration determination apparatus 6 determines whether the combustion state of the internal combustion engine 7 is the fuel-cut state and the reducing agent supply apparatus 73 is injecting a predetermined amount of aqueous urea, (step S101 in FIG. 13). Here, in this determination, various other methods described above can be used to select the case in which ammonia is detected.

Next, when the combustion state of the internal combustion engine 7 is the fuel-cut state and the reducing agent supply apparatus 73 is injecting the predetermined amount of aqueous urea, the deterioration determination apparatus 6 recognizes the initial time for the deterioration determination (step S102). Then, at the initial time, the potential difference detecting unit 51 detects the potential difference ΔV between the ammonia electrode 22 and the reference electrode 23 as the detected voltage value (step S103).

Next, the voltage applying unit 61 applies the DC voltage E of a predetermined applied voltage value between the ammonia electrode 22 and the reference electrode 23. The current detecting unit 62 detects the DC current that flows between the ammonia electrode 22 and the reference electrode 23 as the first sensor current I1 (step S104). Next, the deterioration determining unit 63 determines the first difference ΔI that is obtained by the detected voltage value being subtracted from the applied voltage value. In addition, the deterioration determining unit 63 divides the first sensor current I1 by the first difference ΔF, and determines the first evaluation value H1 (step S105).

Here, the first evaluation value H1 can be stored in the deterioration determination apparatus 6 as a map unit 59, as a value that is common among ammonia sensors 1 of an identical specification. A case in which this map unit 59 is used will be described according to a second embodiment. In addition, "a" in FIG. 13 indicates that the flowchart continues at "a" in FIG. 14.

Figure 14:
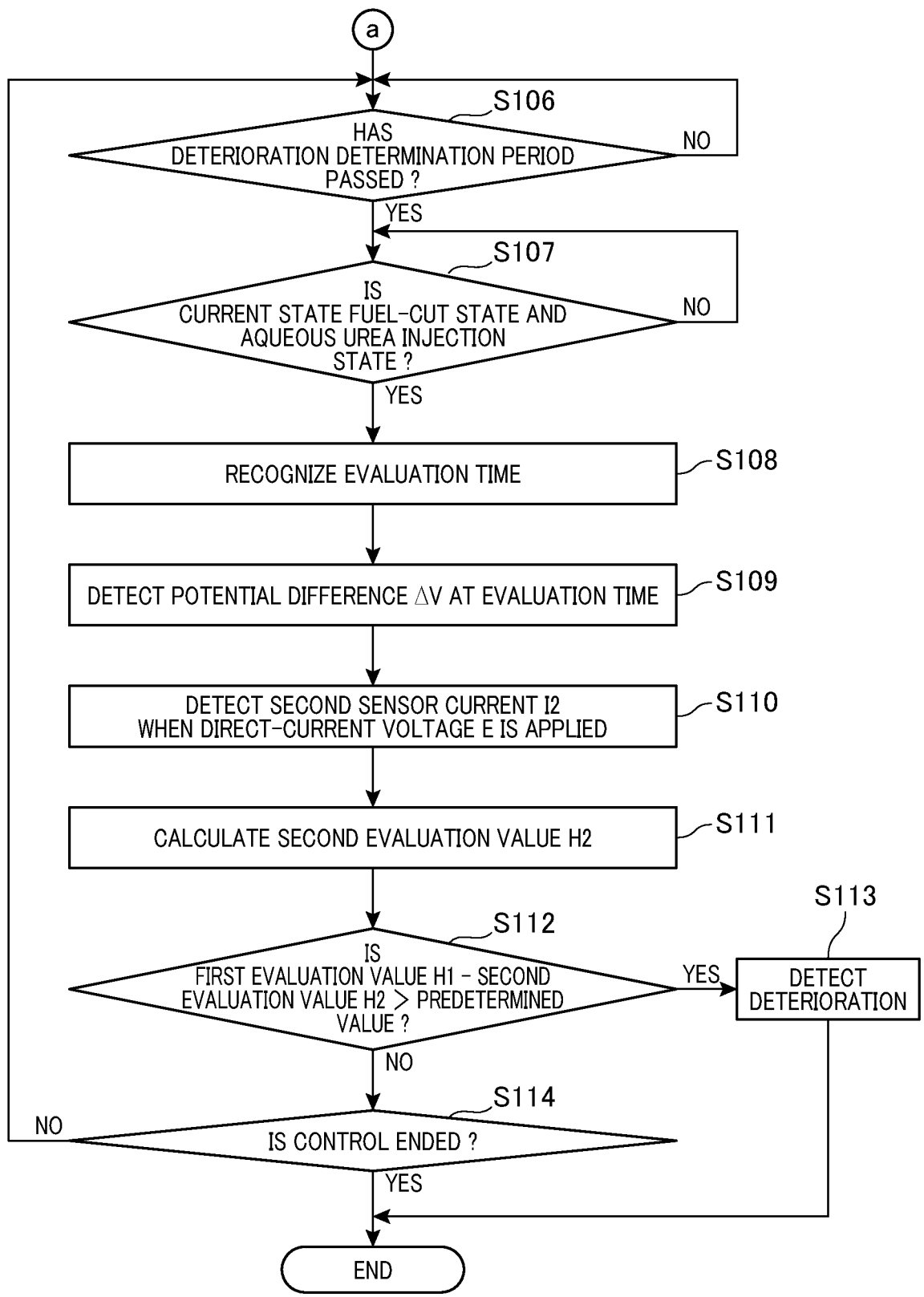
FIG. 14 is a flowchart of the deterioration determination method of the deterioration determination apparatus, according to the first embodiment.

Next, to detect that the ammonia sensor 1 has been used for a predetermined period, the deterioration determination apparatus 6 determines whether a usage period of the ammonia sensor 1 passes a predetermined deterioration determination period (step S106 in FIG. 14). The determination regarding the deterioration determination period can be determined based on whether a traveling distance of a vehicle has reached a predetermined traveling distance. In addition, when the usage period of the ammonia sensor 1 exceeds the predetermined deterioration determination period, the deterioration determination apparatus 6 determines whether the combustion state of the internal combustion engine 1 is the fuel-cut state and the reducing agent supply apparatus 73 is injecting the predetermined amount of aqueous urea (step S107).

Next, when the combustion state of the internal combustion engine 1 is the fuel-cut state and the reducing agent supply apparatus 73 is injecting the predetermined amount of aqueous urea, the deterioration determination apparatus 6 recognizes the evaluation time for the deterioration determination (step S108). As a result of recognition of the evaluation time, the ammonia concentration in the measured gas G at the evaluation time can be substantially identical to the ammonia concentration when the first evaluation value H1 is determined at the initial time.

Then, at the evaluation time, the potential difference detecting unit 51 detects the potential difference ΔV between the ammonia electrode 22 and the reference electrode 23 as the detected voltage value (step S109).

Next, the voltage applying unit 61 applies the DC voltage E of the predetermined applied voltage value between the ammonia electrode 22 and the reference electrode 23. The current detecting unit 62 detects the DC current that flows between the ammonia electrode 22 and the reference electrode 23 as the second sensor current I2 (step S110).

Next, the deterioration determining unit 63 determines the second difference ΔF that is obtained by the detected voltage value being subtracted from the applied voltage value. In addition, the deterioration determining unit 63 divides the second sensor current I2 by the second difference ΔE, and determines the second evaluation value H2 (step S111).

Next, the deterioration determining unit 63 compares the gradient θ1 that is based on the first evaluation value H1 and the gradient θ2 that is based on the second evaluation value H2, and determines whether the gradient θ2 that is based on the second evaluation value H2 is less than the gradient θ1 that is based on the first evaluation value H1 by an amount exceeding a predetermined value (step S112).

When the gradient θ2 that is based on the second evaluation value H2 is less than the gradient θ1 that is based on the first evaluation value H1 by an amount exceeding the predetermined value, the deterioration determining unit 63 detects that deterioration has occurred in the ammonia element portion 2 (step S113).

Here, the predetermined value is a threshold for determining deterioration and can be changed as appropriate based on the setting of the degree of deterioration when deterioration is detected. In addition, instead of the presence/absence of deterioration being detected or in addition to the presence/absence of deterioration being detected, a deterioration rate that indicates an extent by which the gradient that is based on the second evaluation value H2 is less than the gradient that is based on the first evaluation value H1 can be detected.

When the gradient θ2 that is based on the second evaluation value H2 is not less than the gradient θ1 that is based on the first evaluation value H1 by an amount exceeding the predetermined value, the deterioration determination apparatus 6 determines whether a signal to end control of the ammonia sensor 1 is present (step 114). When the signal to end control is present, the deterioration determination apparatus 6 ends control of ammonia sensor 1. Meanwhile, when the signal to end control is not present, the deterioration determination apparatus 6 returns to step S106 and repeatedly performs steps S106 to S114 again based on the traveling distance of the vehicle and the like.

Here, when the deterioration determination apparatus 6 returns to step S106, the usage period of the ammonia sensor 1 can be reset. In this case, at step S106, the determination operation regarding deterioration is on standby until the usage period of the ammonia sensor 1 again exceeds the deterioration determination period. In this case, the determination operation regarding deterioration can be performed every time a predetermined traveling distance is passed.

In addition, the predetermined deterioration determination period when the deterioration determination apparatus 6 returns to step S106 can also be set to be shorter than the deterioration determination period during the determination at a first step S106.

Working Effects

The deterioration determination apparatus 6 for the ammonia sensor 1 according to the present embodiment is used in the mixed-potential-type ammonia sensor 1. The deterioration determination apparatus 6 determines whether deterioration has occurred in the ammonia element portion 2 of the ammonia sensor 1 using the sensor currents I1 and I2 that flow to the ammonia element portion 2 as a result of application of the DC voltage E.

The deterioration determination apparatus 6 includes the voltage applying unit 61, the current detecting unit 62, and the deterioration determining unit 63. In the deterioration determining unit 63, at the initial time that is the initial period of use of the ammonia sensor 1, and the evaluation time that is subsequent to the initial period of use, the sensor currents that are obtained when the DC voltage E of the same magnitude is applied are detected and compared. Whether deterioration has occurred in the ammonia element portion 2 is determined at the evaluation time or subsequent to the evaluation time.

The mixed-potential-type ammonia sensor 1 is ordinarily used without a voltage being applied between the ammonia electrode 22 and the reference electrode 23, when used to detect the ammonia concentration. At this time, a minute current for detecting the potential difference $\Delta V$ between the ammonia electrode 22 and the reference electrode 23 flows therebetween.

In addition, at the initial time and at the evaluation time, when the voltage applying unit 61 applies the DC voltage E between the ammonia electrode 22 and the reference electrode 23, movement of oxygen ions (oxide ions) suddenly occurs between the ammonia electrode 22 and the reference electrode 23 through the first solid electrolyte 21. The sensor currents I1 and I2 flow between the ammonia electrode 22 and the reference electrode 23.

As a result of the DC voltage E being applied between the ammonia electrode 22 and the reference electrode 23 by the voltage applying unit 61, performance of the ammonia element portion 2 can be reflected in the magnitudes of the sensor currents I1 and I2. According to the present embodiment, in particular, to determine the presence/absence or the degree of deterioration in the oxidation performance of ammonia, the DC voltage E is applied to the ammonia electrode 22 such that the reference electrode 23 is the negative side, as a direction that promotes the oxidation reaction of ammonia, in a state in which the measured gas G contains ammonia.

As a result, particularly in cases in which deterioration has occurred in the ammonia electrode 22 as a result of poisoning or the like, the second sensor current I1 at the evaluation time becomes less than the first sensor current I1 at the initial time. Therefore, in the deterioration determining unit 63, as a result of the extent of change in the second evaluation value H2 that is based on the second sensor current I2 compared to the first evaluation value H2 that is based on the first sensor current I1 being recognized, whether deterioration has occurred in the ammonia element portion 2 can be appropriately determined.

Consequently, using the deterioration determination apparatus 6 for the ammonia sensor 1 according to the present embodiment, whether deterioration has occurred in the ammonia element portion 2 of the mixed-potential-type ammonia sensor 1 can be appropriately determined.

Second Embodiment

According to a present embodiment, a case in which the first evaluation value H1 at the initial time is determined based on a relationship map M that is stored in the deterioration determination apparatus 6 is described.

Figure 15:
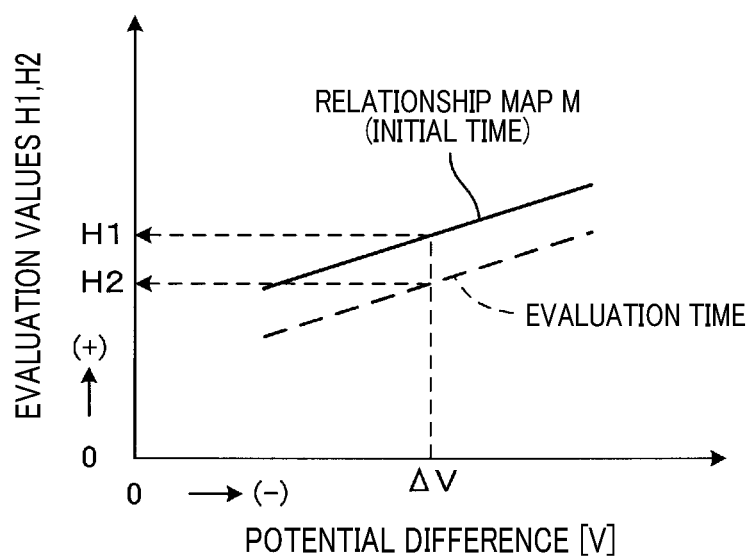
FIG. 15 is an explanatory diagram of a relationship map of potential difference and the first evaluation value, according to a second embodiment.

As shown in FIG. 1 and FIG. 15, the deterioration determination apparatus 6 according to the present embodiment further includes the map unit 59 in which the relationship between the potential difference $\Delta V$ and the first evaluation value H1 is determined as the relationship map M. The relationship map M is generated based on the first evaluation values H1 at a plurality of instances in which the potential difference $\Delta V$ detected by the potential difference detecting unit 51 differs, during testing before the ammonia sensor 1 is actually used, as the initial time of the ammonia sensor 1.

During testing of the ammonia sensor 1, when the relationship map M is generated, the voltage applying unit 61 applies the DC voltage E between the ammonia electrode 22 and the reference electrode 23 and measures the first sensor current I1, for the plurality of instances in which the potential difference $\Delta V$ detected by the potential difference detecting unit 51 differs. Then, for each potential difference $\Delta V$, the first evaluation value H1 is determined using the detected voltage value that is the potential difference $\Delta V$, the applied voltage value that is the DC voltage E, and the measured first sensor current I1. In this manner, regression analysis or the like is performed for each potential difference $\Delta V$ and each first evaluation value H1, and the relationship map M is determined.

As shown in FIG. 15, immediately before the voltage applying unit 61 applies the DC voltage E at the evaluation time, the deterioration determining unit 63 collates the potential difference $\Delta V$ detected by the potential difference detecting unit 51 with the relationship map M, and reads the first evaluation value H1 at the potential difference $\Delta V$ from the relationship map M. The first evaluation value H1 is that determined regarding the ammonia element portion 2 in which deterioration has not occurred.

In addition, the deterioration determining unit 63 compares the first evaluation value H1 and the second evaluation value H2 based on the second sensor current I2, and determines the presence/absence or the degree of deterioration of the ammonia element portion 2, based on the extent of change in the second evaluation value H2 compared to the first evaluation value H1.

The relationship map M can also be determined as a relationship between the potential difference $\Delta V$ and the first sensor current I1. In this case, the deterioration determining unit 63 collates the potential difference $\Delta V$ with the relationship map M, and reads the first sensor current I1 at the potential difference $\Delta V$. Then, the deterioration determining unit 63 determines the first evaluation value H1 using the first sensor current I1, the detected voltage value that is the potential difference $\Delta V$, and the applied voltage value that is the DC voltage E.

In addition, the relationship map M can also be determined as a relationship between the ammonia concentration calculated by the ammonia concentration calculating unit 52, and the first sensor current I1 or the first evaluation value H1. Either of the ammonia concentration before correction based on the oxygen concentration and the ammonia concentration corrected based on the oxygen concentration can be used as the ammonia concentration. As a result of the ammonia concentration corrected based on the oxygen concentration being used, determination accuracy regarding deterioration can be improved.

(Deterioration Determination Method)

Next, a method for performing deterioration determination control using the deterioration determination apparatus 6 according to the preset embodiment will be described with reference to a flowchart in FIG. 16.

When the relationship map M of the potential difference and the first evaluation value H1 is determined, the voltage applying unit 61 applies the DC voltage E between the ammonia electrode 22 and the reference electrode 23, and the current detecting unit 62 detects the first sensor current I1, at a plurality of points in time at which the potential differences ΔV detected by the potential difference detecting unit 51 differ as appropriate. The DC voltage E that is applied is fixed at all times when the potential differences ΔV of a plurality of magnitudes are detected.

In addition, regarding the respective first sensor currents I1 when the potential differences ΔV of a plurality of magnitudes are detected, each first sensor current I1 is divided by the first difference ΔF that is obtained by the detected voltage value that is the detected potential difference ΔV being subtracted from the applied voltage value that is the applied DC voltage E, and the gradient θ1 that serves as the first evaluation value H1 is determined. Furthermore, a relational expression is generated by regression analysis or the like is performed for the relationship between each potential difference ΔV and each first evaluation value H1. The relational expression is stored as the relationship map M.

Figure 16:
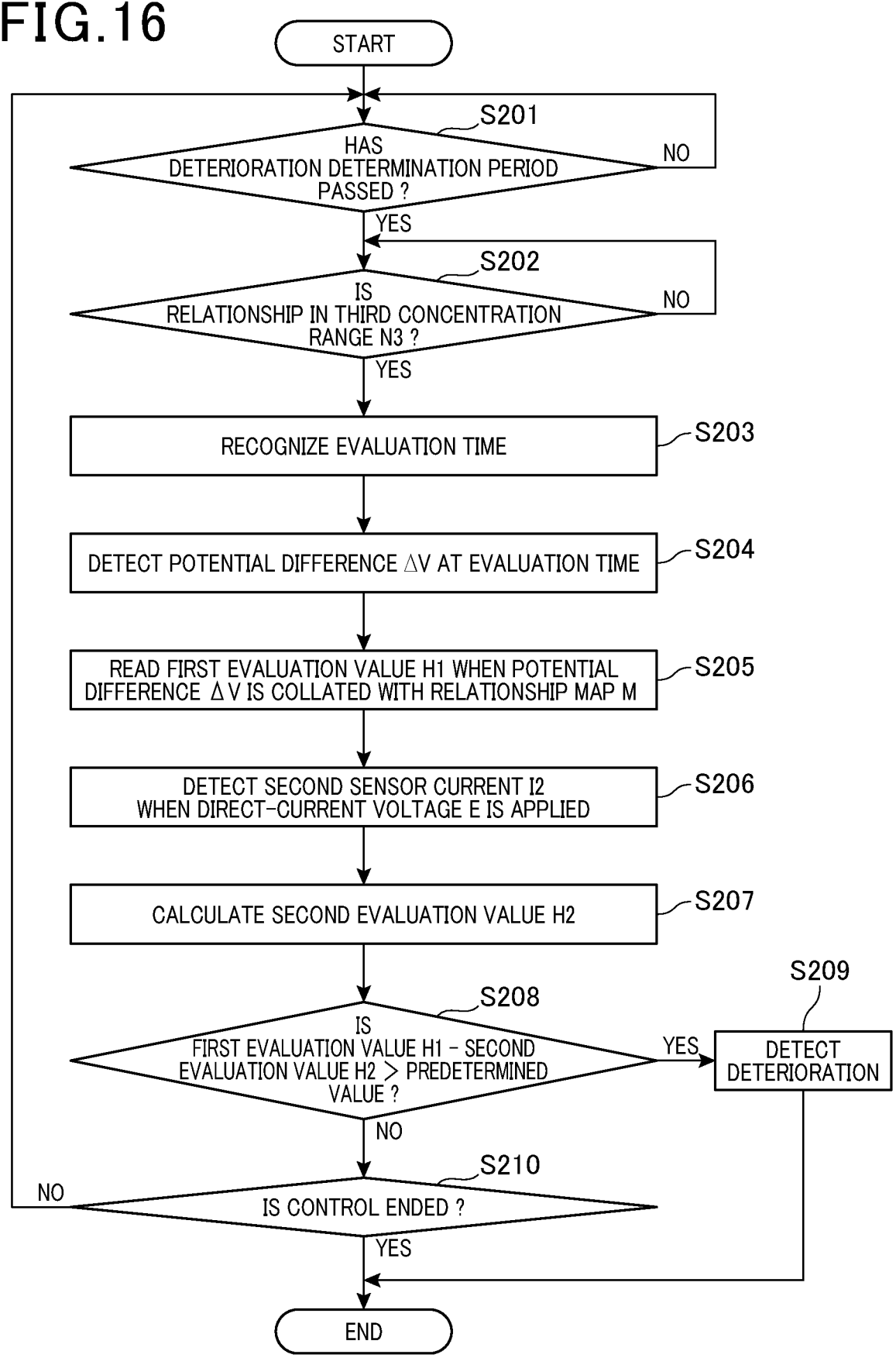
FIG. 16 is a flowchart of a deterioration determination method of the deterioration determination apparatus, according to the second embodiment.

Next, to detect that the ammonia sensor 1 is used over a predetermined period when the ammonia sensor 1 is used, whether the usage period of the ammonia sensor 1 has passed the predetermined deterioration determination period is determined (step S201 in FIG. 16). The determination regarding the deterioration determination period can be determined based on whether the traveling distance of the vehicle has reached a predetermined traveling distance.

In addition, when the usage period of the ammonia sensor 1 passes the predetermined deterioration determination period, the deterioration determination apparatus 6 determines whether the relationship between the ammonia concentration calculated by the ammonia concentration calculating unit 52 and the post-correction $NO_X$ concentration calculated by the $NO_X$ concentration calculating unit 57 is in the third concentration range N3, to select a case in which ammonia is detected by the ammonia sensor 1 (step S202). Here, in this determination, various other methods described above can be used to select the case in which ammonia is detected.

Next, when the relationship between the ammonia concentration and the post-correction $NO_X$ concentration is in the third concentration range N3, the deterioration determination apparatus 6 recognizes the evaluation time for the deterioration determination (step S203). Then, at the evaluation time, the potential difference detecting unit 51 detects the potential difference ΔV between the ammonia electrode 22 and the reference electrode 23 as the detected voltage value (step S204).

Next, the deterioration determination apparatus 6 collates the potential difference ΔV with the relationship map M, and reads the gradient θ1 that serves as the first evaluation value H1 at the initial time at the potential difference ΔV from the relationship map M (step S205).

Next, the voltage applying unit 61 applies the DC voltage E of a predetermined applied voltage value between the ammonia electrode 22 and the reference electrode 23. The current detecting unit 62 detects the DC current that flows between the ammonia electrode 22 and the reference electrode 23 as the second sensor current I2 (step S206).

Next, the deterioration determining unit 63 determines the second difference ΔF that is obtained by the detected voltage value being subtracted from the applied voltage value. In addition, the deterioration determining unit 63 divides the second sensor current I2 by the second difference ΔE, and determines the gradient θ2 that serves as the second evaluation value H2 (step S207).

Next, the deterioration determining unit 63 compares the gradient θ1 that is based on the first evaluation value H1 and the gradient θ2 that is based on the second evaluation value H2, and determines whether the gradient θ2 that is based on the second evaluation value H2 is less than the gradient θ1 that is based on the first evaluation value H1 by an amount exceeding a predetermined value (step S208).

When the gradient θ2 that is based on the second evaluation value H2 is less than the gradient θ1 that is based on the first evaluation value H1 by an amount exceeding the predetermined value, the deterioration determining unit 63 detects that deterioration has occurred in the ammonia element portion 2 (step S209).

When the gradient θ2 that is based on the second evaluation value H2 is not less than the gradient θ1 that is based on the first evaluation value H1 by an amount exceeding the predetermined value, the deterioration determination apparatus 6 determines whether a signal to end control of the ammonia sensor 1 is present (step 210).

When the signal to end control is present, the deterioration determination apparatus 6 ends control of ammonia sensor 1. Meanwhile, when the signal to end control is not present, the deterioration determination apparatus 6 returns to step S201 and repeatedly performs steps S201 to S210 again based on the traveling distance of the vehicle and the like.

According to the present embodiment, the relationship map M is required to be generated. However, as a result of the relationship map M being used, determination accuracy of the deterioration determining unit 63 regarding deterioration can be easily improved. Other configurations, the deterioration determination method, working effects, and the like of the deterioration determination apparatus 6 according to the present embodiment are similar to those according to the first embodiment. In addition, according to the present embodiment as well, constituent elements indicated by reference numbers that are identical to those according to the first embodiment are similar to those according to the first embodiment.

The present disclosure is not only limited to the embodiments. Further differing embodiments are also possible without departing from the spirit of the invention. In addition, the present disclosure includes various modification examples, modification examples within the range of equivalency, and the like.

What is claimed is:

1. A deterioration determination apparatus for an ammonia sensor, the deterioration determination apparatus being configured to be usable with an ammonia sensor that includes
    an ammonia element portion that includes
        a solid electrolyte that has oxygen ion conductivity,
        an ammonia electrode that is provided on a first surface of the solid electrolyte that is exposed to a measured gas that contains oxygen and ammonia, and
        a reference electrode that is provided on a second surface of the solid electrolyte on a side opposite the first surface,
    a potential difference detecting unit that detects a potential difference between the ammonia electrode and the reference electrode, and
    an ammonia concentration calculating unit that calculates an ammonia concentration in the measured gas based on the potential difference detected by the potential difference detecting unit, the deterioration determination apparatus comprising:
- a voltage applying unit that applies a DC voltage between the ammonia electrode and the reference electrode;
- a current detecting unit that detects a DC current that flows between the ammonia electrode and the reference electrode; and
- a deterioration determining unit that compares a first evaluation value and a second evaluation value, and determines whether deterioration has occurred in the ammonia element portion at an evaluation time or subsequent to the evaluation time,
  - the first evaluation value being based on a first sensor current that is a DC current that is detected by the current detecting unit obtained when the voltage applying unit applies a DC voltage between the ammonia electrode and the reference electrode at an initial time that is during an initial use period of the ammonia sensor, and
  - the second evaluation value being based on a second sensor current that is a DC current that is detected by the current detecting unit obtained when the voltage applying unit applies a DC voltage of a same magnitude as that at the initial time between the ammonia electrode and the reference electrode at the evaluation time that is subsequent to the initial usage period of the ammonia sensor; and
- a map unit in which a relationship between the potential difference or the ammonia concentration, and the first sensor current is determined as a relationship map, based on the first sensor currents at a plurality of instances in which the potential difference detected by the potential difference detecting unit or the ammonia concentration calculated by the ammonia concentration calculating unit varies, at the initial time, wherein
- the deterioration determining unit is configured to
  - collate the potential difference detected by the potential difference detecting unit or the ammonia concentration calculated by the ammonia concentration calculating unit with the relationship map, read the first sensor current at the potential difference or the ammonia concentration from the relationship map, and determine the first evaluation value, before the voltage applying unit applies the DC voltage at the evaluation time, and
  - compare the first evaluation value and the second evaluation value that is based on the second sensor current.

2. The deterioration determination apparatus for an ammonia sensor according to claim 1, wherein:
  - the voltage applying unit is configured to apply the DC voltage between the ammonia electrode and the reference electrode with the reference electrode as a negative side;
  - the initial time in the deterioration determining unit is set to be during the initial period of use of the ammonia sensor and when the ammonia concentration calculated by the ammonia concentration calculating unit is a concentration that indicates detection of ammonia; and
  - the evaluation time in the deterioration determining unit is set to be subsequent to the initial period of use of the ammonia sensor and when the ammonia concentration calculated by the ammonia concentration calculating unit is a concentration that indicates detection of ammonia.

3. The deterioration determination apparatus for an ammonia sensor according to claim 1, wherein:
  - the deterioration determining unit is configured to
    - determine a plurality of second evaluation values with a plurality of points in time at which the ammonia concentration calculated by the ammonia concentration calculating unit differs as the evaluation time, and
    - successively compare the first evaluation value and each of the plurality of evaluation values, and determine whether deterioration has occurred in the ammonia element portion.

4. The deterioration determination apparatus for an ammonia sensor according to claim 1, wherein:
  - the deterioration determining unit determines the initial time and the evaluation time when the ammonia concentration calculated by the ammonia concentration calculating unit being a concentration that indicates detection of ammonia and a concentration that is equal to or less than 200 parts per million.

5. The deterioration determination apparatus for an ammonia sensor according to claim 1, wherein:
  - in an exhaust pipe of an internal combustion engine in which a catalyst that reduces $NO_X$ and a reducing agent supply apparatus that supplies a reducing agent that contains ammonia to the catalyst are arranged, the ammonia sensor detects a concentration of ammonia that flows out from the catalyst; and
  - the deterioration determining unit determines the initial time and the evaluation time in a period during which the reducing agent is supplied to the catalyst by the reducing agent supply apparatus.

6. A deterioration determination apparatus for an ammonia sensor, the deterioration determination apparatus being configured to be usable with an ammonia sensor that includes
  - an ammonia element portion that includes
    - a solid electrolyte that has oxygen ion conductivity,
    - an ammonia electrode that is provided on a first surface of the solid electrolyte that is exposed to a measured gas that contains oxygen and ammonia, and
    - a reference electrode that is provided on a second surface of the solid electrolyte on a side opposite the first surface,
  - a potential difference detecting unit that detects a potential difference between the ammonia electrode and the reference electrode, and
  - an ammonia concentration calculating unit that calculates an ammonia concentration in the measured gas based on the potential difference detected by the potential difference detecting unit,
  - the deterioration determination apparatus comprising:
    - a voltage applying unit that applies a DC voltage between the ammonia electrode and the reference electrode;
    - a current detecting unit that detects a DC current that flows between the ammonia electrode and the reference electrode;
    - a deterioration determining unit that compares a first evaluation value and a second evaluation value, and determines whether deterioration has occurred in the ammonia element portion at an evaluation time or subsequent to the evaluation time,
      - the first evaluation value being based on a first sensor current that is a DC current that is detected by the current detecting unit obtained when the voltage applying unit applies a DC voltage between the ammonia electrode and the reference electrode at an initial time that is during an initial use period of the ammonia sensor, and the second evaluation value being based on a second sensor current that is a DC current that is detected by the current detecting unit obtained when the voltage applying unit applies a DC voltage of a same magnitude as that at the initial time between the ammonia electrode and the reference electrode at the evaluation time that is subsequent to the initial usage period of the ammonia sensor; and a map unit in which a relationship between the potential difference or the ammonia concentration, and the first evaluation value is determined as a relationship map, based on the first evaluation values at a plurality of instances in which the potential difference detected by the potential difference detecting unit or the ammonia concentration calculated by the ammonia concentration calculating unit differs, at the initial time and, wherein the deterioration determining unit is configured to collate the potential difference detected by the potential difference detecting unit or the ammonia concentration calculated by the ammonia concentration calculating unit with the relationship map, and read the first evaluation value at the potential difference or the ammonia concentration from the relationship map, before the voltage applying unit applies the DC voltage at the evaluation time, and compare the first evaluation value and the second evaluation value that is based on the second sensor current.

7. A deterioration determination apparatus for an ammonia sensor, the deterioration determination apparatus being configured to be usable with an ammonia sensor that includes an ammonia element portion that includes a solid electrolyte that has oxygen ion conductivity, an ammonia electrode that is provided on a first surface of the solid electrolyte that is exposed to a measured gas that contains oxygen and ammonia, and a reference electrode that is provided on a second surface of the solid electrolyte on a side opposite the first surface, a potential difference detecting unit that detects a potential difference between the ammonia electrode and the reference electrode, and an ammonia concentration calculating unit that calculates an ammonia concentration in the measured gas based on the potential difference detected by the potential difference detecting unit, the deterioration determination apparatus comprising:

a voltage applying unit that applies a DC voltage between the ammonia electrode and the reference electrode;

a current detecting unit that detects a DC current that flows between the ammonia electrode and the reference electrode; and a deterioration determining unit that compares a first evaluation value and a second evaluation value, and determines whether deterioration has occurred in the ammonia element portion at an evaluation time or subsequent to the evaluation time, the first evaluation value being based on a first sensor current that is a DC current that is detected by the current detecting unit obtained when the voltage applying unit applies a DC voltage between the ammonia electrode and the reference electrode at an initial time that is during an initial use period of the ammonia sensor, and the second evaluation value being based on a second sensor current that is a DC current that is detected by the current detecting unit obtained when the voltage applying unit applies a DC voltage of a same magnitude as that at the initial time between the ammonia electrode and the reference electrode at the evaluation time that is subsequent to the initial usage period of the ammonia sensor, wherein the deterioration determining unit is configured to determine the first evaluation value based on a first difference and the first sensor current, the first difference being obtained by a detected voltage value that is the potential difference detected by the potential difference detecting unit before the voltage applying unit applies the DC voltage at the initial time being subtracted from an applied voltage value that is the DC voltage applied by the voltage applying unit at the initial time, and determine the second evaluation value based on a second difference and the second sensor current, the second sensor current being obtained by a detected voltage value that is the potential difference detected by the potential difference detecting unit before the voltage applying unit applies the DC voltage at the evaluation time being subtracted from an applied voltage value that is the DC voltage applied by the voltage applying unit at the evaluation time.

8. The deterioration determination apparatus for an ammonia sensor according to claim 7, wherein:

the deterioration determining unit is configured to determine the first evaluation value based on an area that is obtained by multiplication of a gradient or the first sensor current, and the first difference, the gradient being obtained by the first sensor current being divided by the first difference, and determine the second evaluation value based on an area that is obtained by multiplication of a gradient or the second sensor current, and the second difference, the gradient being obtained by the second sensor current being divided by the second difference.

9. A deterioration determination apparatus for an ammonia sensor, the deterioration determination apparatus being configured to be usable with an ammonia sensor that includes an ammonia element portion that includes a solid electrolyte that has oxygen ion conductivity, an ammonia electrode that is provided on a first surface of the solid electrolyte that is exposed to a measured gas that contains oxygen and ammonia, and a reference electrode that is provided on a second surface of the solid electrolyte on a side opposite the first surface, a potential difference detecting unit that detects a potential difference between the ammonia electrode and the reference electrode, and an ammonia concentration calculating unit that calculates an ammonia concentration in the measured gas based on the potential difference detected by the potential difference detecting unit, the deterioration determination apparatus comprising:

a voltage applying unit that applies a DC voltage between the ammonia electrode and the reference electrode;

a current detecting unit that detects a DC current that flows between the ammonia electrode and the reference electrode; and a deterioration determining unit that compares a first evaluation value and a second evaluation value, and determines whether deterioration has occurred in the ammonia element portion at an evaluation time or subsequent to the evaluation time, the first evaluation value being based on a first sensor current that is a DC current that is detected by the current detecting unit obtained when the voltage applying unit applies a DC voltage between the ammonia electrode and the reference electrode at an initial time that is during an initial use period of the ammonia sensor, and the second evaluation value being based on a second sensor current that is a DC current that is detected by the current detecting unit obtained when the voltage applying unit applies a DC voltage of a same magnitude as that at the initial time between the ammonia electrode and the reference electrode at the evaluation time that is subsequent to the initial usage period of the ammonia sensor, wherein:

in an exhaust pipe of an internal combustion engine in which a catalyst that reduces $NO_X$ and a reducing agent supply apparatus that supplies a reducing agent that contains ammonia to the catalyst are arranged, the ammonia sensor detects a concentration of ammonia that flows out from the catalyst; and the deterioration determining unit determines the initial time and the evaluation time in a period during which a fuel-cut operation is performed by the internal combustion engine and the reducing agent is supplied to the catalyst by the reducing agent supply apparatus.

10. A deterioration determination apparatus for an ammonia sensor, the deterioration determination apparatus being configured to be usable with an ammonia sensor that includes an ammonia element portion that includes a solid electrolyte that has oxygen ion conductivity, an ammonia electrode that is provided on a first surface of the solid electrolyte that is exposed to a measured gas that contains oxygen and ammonia, and a reference electrode that is provided on a second surface of the solid electrolyte on a side opposite the first surface, a potential difference detecting unit that detects a potential difference between the ammonia electrode and the reference electrode, and an ammonia concentration calculating unit that calculates an ammonia concentration in the measured gas based on the potential difference detected by the potential difference detecting unit, the deterioration determination apparatus comprising:

a voltage applying unit that applies a DC voltage between the ammonia electrode and the reference electrode;

a current detecting unit that detects a DC current that flows between the ammonia electrode and the reference electrode; and a deterioration determining unit that compares a first evaluation value and a second evaluation value, and determines whether deterioration has occurred in the ammonia element portion at an evaluation time or subsequent to the evaluation time, the first evaluation value being based on a first sensor current that is a DC current that is detected by the current detecting unit obtained when the voltage applying unit applies a DC voltage between the ammonia electrode and the reference electrode at an initial time that is during an initial use period of the ammonia sensor, and the second evaluation value being based on a second sensor current that is a DC current that is detected by the current detecting unit obtained when the voltage applying unit applies a DC voltage of a same magnitude as that at the initial time between the ammonia electrode and the reference electrode at the evaluation time that is subsequent to the initial usage period of the ammonia sensor, wherein:

the potential difference detecting unit is configured to detect the potential difference between the ammonia electrode and the reference electrode that is generated when a reduction reaction of oxygen and an oxidation reaction of ammonia in the ammonia electrode become equal;

the ammonia sensor further includes a $NO_X$ element portion that includes a second solid electrolyte that has oxygen ion conductivity and is arranged so as to oppose the solid electrolyte, a measured gas chamber that is formed so as to be in contact with a third surface of the second solid electrolyte, a diffusion resistance portion that introduces the measured gas to the measured gas chamber while limiting a diffusion speed, a pump electrode that is provided in a position inside the measured gas chamber on the third surface, a $NO_X$ electrode that is provided in a position inside the measured gas chamber on the third surface, and one or a plurality of second reference electrodes that are provided on a fourth surface of the second solid electrolyte on a side opposite the third surface, a pump unit that applies a DC voltage between the pump electrode and the other reference electrode with the second reference electrode as a positive side, and pumps out oxygen in the measured gas inside the measured gas chamber, a pump current detecting unit that detects a DC current that flows between the pump electrode and the other reference electrode, an oxygen concentration calculating unit that calculates an oxygen concentration in the measured gas based on the DC current detected by the pump current detecting unit, a $NO_X$ detecting unit that applies a DC voltage between the $NO_X$ electrode and the other reference electrode with the other reference electrode as the positive side, and detects the DC current that flows between the $NO_X$ electrode and the other reference electrode, and a $NO_X$ concentration calculating unit that calculates a $NO_X$ concentration in the measured gas based on the DC current detected by the $NO_X$ detecting unit, and the ammonia concentration calculating unit is configured to correct the ammonia concentration based on at least either of the oxygen concentration calculated by the oxygen concentration calculating unit and the $NO_X$ concentration calculated by the $NO_X$ concentration calculating unit.

* * * * *